(12) United States Patent
Rakow et al.

(10) Patent No.: US 7,553,670 B2
(45) Date of Patent: Jun. 30, 2009

(54) METHOD FOR MONITORING A POLYMERIZATION IN A THREE-DIMENSIONAL SAMPLE

(75) Inventors: Neal A. Rakow, Woodbury, MN (US);
Rajdeep S. Kalgutkar, St. Paul, MN (US); Duane D. Fansler, Dresser, WI (US); Eric R. Jackson, Woodbury, MN (US); Stephen B. Roscoe, St. Paul, MN (US)

(73) Assignee: 3M Innovative Properties Company, St. Paul, MN (US)

( * ) Notice: Subject to any disclaimer, the term of this patent is extended or adjusted under 35 U.S.C. 154(b) by 972 days.

(21) Appl. No.: 10/834,305

(22) Filed: Apr. 28, 2004

(65) Prior Publication Data

US 2005/0244975 A1   Nov. 3, 2005

(51) Int. Cl.
*G01N 33/00* (2006.01)
*G01N 25/20* (2006.01)
*G01N 33/22* (2006.01)
*G01N 33/44* (2006.01)

(52) U.S. Cl. .......................... 436/34; 436/147; 436/37; 436/85

(58) Field of Classification Search ............... 436/85, 436/171, 34, 147
See application file for complete search history.

(56) References Cited

U.S. PATENT DOCUMENTS

| | | | |
|---|---|---|---|
| 3,066,112 A | 11/1962 | Bowen | |
| 3,524,983 A | 8/1970 | Voelz | |
| 3,539,533 A | 11/1970 | Lee II, et al. | |
| 3,629,187 A | 12/1971 | Waller | |
| 3,708,296 A | 1/1973 | Schlesinger | |
| 3,709,866 A | 1/1973 | Waller | |
| 3,751,399 A | 8/1973 | Lee Jr. et al. | |
| 3,766,132 A | 10/1973 | Lee Jr. et al. | |
| 3,860,556 A | 1/1975 | Taylor | |
| 3,987,037 A | 10/1976 | Bonham et al. | |
| 4,002,669 A | 1/1977 | Gross et al. | |
| 4,069,055 A | 1/1978 | Crivello | |
| 4,071,424 A | 1/1978 | Dart et al. | |
| 4,115,346 A | 9/1978 | Gross et al. | |
| 4,216,288 A | 8/1980 | Crivello | |
| 4,250,311 A | 2/1981 | Crivello | |
| 4,259,117 A | 3/1981 | Yamauchi et al. | |
| 4,292,029 A | 9/1981 | Craig et al. | |
| 4,308,190 A | 12/1981 | Walkowiak et al. | |
| 4,327,014 A | 4/1982 | Kawahara et al. | |
| 4,379,695 A | 4/1983 | Orlowski et al. | |

(Continued)

FOREIGN PATENT DOCUMENTS

CA    1 300 307    5/1992

(Continued)

OTHER PUBLICATIONS http://64.233.169.104/search?q+cache:2RpaNerzWDcJ:www.mdatechnology.net/techsearch/spin.aspx%3Farticleid%3D187+spinoff+technology+digital+infrared+camera+raytheon&hl=en&gl=us&strip=1.*

(Continued)

*Primary Examiner*—Jill Warden
*Assistant Examiner*—Timothy G Kingan

(57) ABSTRACT

A method of optical infrared thermography, and the use thereof in monitoring and characterizing the polymerization of the three dimensional sample is described.

23 Claims, 3 Drawing Sheets

U.S. PATENT DOCUMENTS

| | | | |
|---|---|---|---|
| 4,387,240 | A | 6/1983 | Berg |
| 4,404,150 | A | 9/1983 | Tsunekawa et al. |
| 4,505,793 | A | 3/1985 | Tamoto et al. |
| 4,582,520 | A | 4/1986 | Sturm |
| 4,587,291 | A | 5/1986 | Gardziella et al. |
| 4,642,126 | A | 2/1987 | Zador et al. |
| 4,652,274 | A | 3/1987 | Boettcher et al. |
| 4,695,251 | A | 9/1987 | Randklev |
| 4,737,593 | A | 4/1988 | Ellrich et al. |
| 4,772,530 | A | 9/1988 | Gottschalk et al. |
| 4,868,288 | A | 9/1989 | Meier |
| 4,874,450 | A | 10/1989 | Gottschalk |
| 4,874,948 | A | 10/1989 | Cielo et al. |
| 4,952,612 | A | 8/1990 | Brown-Wensley et al. |
| 4,954,414 | A | 9/1990 | Adair et al. |
| 4,985,340 | A | 1/1991 | Palazzotto et al. |
| 5,055,372 | A | 10/1991 | Shanklin et al. |
| 5,057,393 | A | 10/1991 | Shanklin et al. |
| 5,073,476 | A | 12/1991 | Meier et al. |
| 5,084,586 | A | 1/1992 | Farooq |
| 5,086,086 | A | 2/1992 | Brown-Wensley et al. |
| 5,089,536 | A | 2/1992 | Palazzotto |
| 5,124,417 | A | 6/1992 | Farooq |
| 5,142,151 | A | 8/1992 | Varnell et al. |
| 5,376,428 | A | 12/1994 | Palazzotto et al. |
| 5,399,637 | A | 3/1995 | Willett et al. |
| 5,539,017 | A | 7/1996 | Rheinberger et al. |
| 5,545,676 | A | 8/1996 | Palazzotto et al. |
| 5,856,373 | A | 1/1999 | Kaisaki et al. |
| 5,876,805 | A | 3/1999 | Ostlie |
| 6,016,190 | A | 1/2000 | Glazman |
| 6,025,406 | A | 2/2000 | Oxman et al. |
| 6,346,290 | B1 | 2/2002 | Schultz et al. |
| 6,444,725 | B1 | 9/2002 | Trom et al. |
| 6,536,944 | B1 | 3/2003 | Archibald et al. |
| 6,541,271 | B1 | 4/2003 | McFarland et al. |
| 6,572,693 | B1 | 6/2003 | Wu et al. |
| 6,605,690 | B1 | 8/2003 | Gross et al. |
| 2003/0195273 | A1 | 10/2003 | Mitra et al. |

FOREIGN PATENT DOCUMENTS

| | | |
|---|---|---|
| CA | 2 316 188 | 6/2000 |
| EP | 0 173 567 A2 | 3/1986 |
| EP | 0 094 914 B1 | 9/1986 |
| GB | 736 457 | 9/1955 |
| GB | 1 247 116 | 9/1971 |
| GB | 2 310 855 A | 9/1997 |
| WO | WO 02/068264 A2 | 9/2002 |
| WO | WO 03/087885 A2 | 10/2003 |

OTHER PUBLICATIONS http://www.palmir250.com/ir250D.htm; Jan. 14, 2009.*

Encyclopedia of Polymer Science and Engineering, (1987), pp. 279-332, vol. 8, John Wiley & Sons, New York.

S. S. Negmatov et al., "Physical Model of the Formation Process of the Incompatible Epoxy-Polyethylene Compositions", (1990), pp. 65-67, vol. 6, CA 115:93689n.

K. Dietlike, "A Compilation of Photoinitiators Commercially Available for UV Today", SITA Technology, (2002), Edinburgh and London, UK.

J.V. Crivello et al., "Photoinitiators for Free Radical Cationic & Anionic Photopolymerisation", $2^{nd}$ Edition, (1998), vol. III, SITA Technology, John Wiley & Sons.

Kirk-Othmer Encyclopedia of Chemical Technology, $4^{th}$ Edition, (1998), pp. 253-255, Index to vol. 1-25 and Supplement, John Wiley and Sons, New York.

J. C. Meredith et al., "High-Throughput Measurement of Polymer Blend Phase Behavior", *Macromolecules*, (Aug. 8, 2000), pp. 5760-5762, vol. 33, No. 16, American Chemical Society.

J. C. Meredith et al., "Combinatorial Materials Science for Polymer Thin-Film Dewetting", *Macromolecules*, (Dec. 26, 2000), pp. 9747-9756, vol. 33, No. 26, American Chemical Society.

M. T. Reetz, et al., "Time-Resolved IR-Thermographic Detection and Screening of Enantioselectivity in Catalytic Reactions", *Angew. Chem. Int. Ed.*, (1998), pp. 2647-2650, vol. 37, No. 19, Wiley-VCH Verlag GmbH, D-69451 Weinheim.

A. Holzwarth, et al., "Detection of Catalytic Activity in Combinatorial Libraries of Heterogeneous Catalysts by IR Thermography", *Angew. Chem. Int. Ed.*, (1998), pp. 2644-2647, vol. 37, No. 19, Wiley-VCH Verlag GmbH, D-69451 Weinheim.

B. Falk, et al., "Monitoring Photopolymerization Reactions with Optical Pyrometry", *Journal of Polymer Science: Part A: Polymer Chemistry*, (2003), pp. 579-596, vol. 41, Wiley Periodicals, Inc.

P. C. Pawlicki, et al., "Spatial Effects on Supported Catalysts", *Chemical Engineering Progress*, (Feb. 1987), pp. 40-45.

J. C. Kellow, et al., "Infrared Thermography and FTIR Studies of Catalyst Preparation Effects on Surface Reaction Dynamics During Co and Ethylene Oxidation on $Rh/SiO_2$ Catalysts", *Chemical Engineering Science*, (1990), pp. 2597-2602, vol. 45, No. 8.

Hussey et al., "*Thermographic Measurement of Temperature Change During Resin Composite Polymerization* in Vivo", Journal of Dentistry, (1995), pp. 267-271, vol. 23, No. 5, Elsevier Science Ltd.

Greenberg et al., "*Use of Infrared Thermography for Temperature Measurement During Evaporative Casting of Thin Polymeric Films*", Journal of Membrane Science, (1995), pp. 249-261, vol. 107, Elsevier Science Ltd.

Rantala et al., "*NDT of Polymer Materials Using Lock-In Thermography With Water-Coupled Ultrasonic Excitation*", NDT&E International, (1998), pp. 43-49, vol. 31, No. 1, Elsevier Science Ltd.

* cited by examiner

METHOD FOR MONITORING A POLYMERIZATION IN A THREE-DIMENSIONAL SAMPLE

The present invention is directed to optical infrared thermography, and the use thereof in monitoring and characterizing the polymerization of a three dimensional sample.

BACKGROUND

Many techniques have been developed for monitoring the course of a polymerization reaction. Infrared spectroscopy (IR) and nuclear magnetic resonance (NMR) have been used to monitor the depletion of monomers and the subsequent production of the product polymers, but these techniques provide little information on the thermodynamics of the reactions studied, particularly the heat evolved. Calorimetry, and differential scanning calorimetry has been used to study the exotherms of polymerization reactions, but these techniques provide information only on the bulk sample per se; it is not possible to obtain information about the thermal characteristics, such as the exothermicity or heat evolution from areas, or regions of a particular sample.

Optical pyrometry has been used effectively for measuring the surface temperatures of various materials, particularly incandescent materials, and in evaluating catalytic activity, reactivity of monomers or other reactants, the rates of reactions, or reaction conditions of thin film samples. Typically a thin film sample is evaluated and the temperatures of the samples are recorded. Higher peak temperatures, for example, have been used to screen various catalysts, with those samples exhibiting higher peak temperatures presumed to have higher catalytic activity under a given set of conditions.

SUMMARY OF THE INVENTION

The present invention provides a method of monitoring a polymerization in a three-dimensional sample comprising initiating said polymerization, and capturing a thermographic profile of said sample with an IR detector array. The method may be used for both thermal- and photo-polymerizations or combinations thereof. The samples comprise an initiation surface where polymerization may be initiated, and one or more monitoring surfaces, where the polymerization is monitored and the thermographic profile of the polymerization captured.

As used herein, a thermogram or thermographic profile refers to the temperature profile of a three-dimensional sample at a plurality of points on one or more surfaces of the sample, i.e. a "temperature map" of a surface. A thermographic profile may be distinguished from the result obtained from single point optical pyrometry, which measures the temperature at a single point, or an average temperature of a surface.

Although optical pyrometry has been used to characterize the polymerization of thin films, it will be appreciated that the behavior of a three-dimensional sample may be markedly different than a thin film sample. Thin films have relatively high surface area, so any heat generated during a polymerization is more effectively dissipated than from a bulk sample. In particular, three-dimensional samples will take longer to reach peak temperatures, and may retain the heat longer due to the greater thermal mass. This may affect, for example, the peak temperatures reached, the degree of polymerization, the degree of shrinkage, the molecular weights of the product polymers, the degree of conversion in crosslinked polymer networks, the molecular weight distribution, the shrinkage, the depth of polymerization, and the number of defects. Additionally, composite polymeric materials are not readily analyzed using thin films.

In one embodiment, the sample comprises one or more thermally polymerizable monomers. The polymerization is initiated by exposure of at least one surface to thermal energy, and the thermographic profile captured. In another embodiment, the sample may comprise one or more photopolymerizable monomers, wherein the polymerization is initiated by exposure to actinic radiation, and the thermographic profile captured. In other embodiments, the thermographic profile may be captured concurrently with one or more additional analytical techniques, such as IR spectroscopy.

Each thermographic profile may be captured at a single point in time, or as a function of time. When captured as a function of time, individual points on a surface of the sample may be analyzed, and the results compared over time. Individual points may be compared at a particular time to determine how the polymerization proceeds through the sample, and how it varies at different points on a sample. Each thermographic profile may comprise multiple points on a single surface of a sample, one or more points on different surfaces of a sample, or one or more points on an array of samples.

The thermographic profile may be used to optimize formulations, curing conditions, depths of cure, the kinetic profile and rate of cure. The thermographic profile may also be used to correlate the post cure-physical and/or chemical properties.

DETAILED DESCRIPTION

Figure 1:
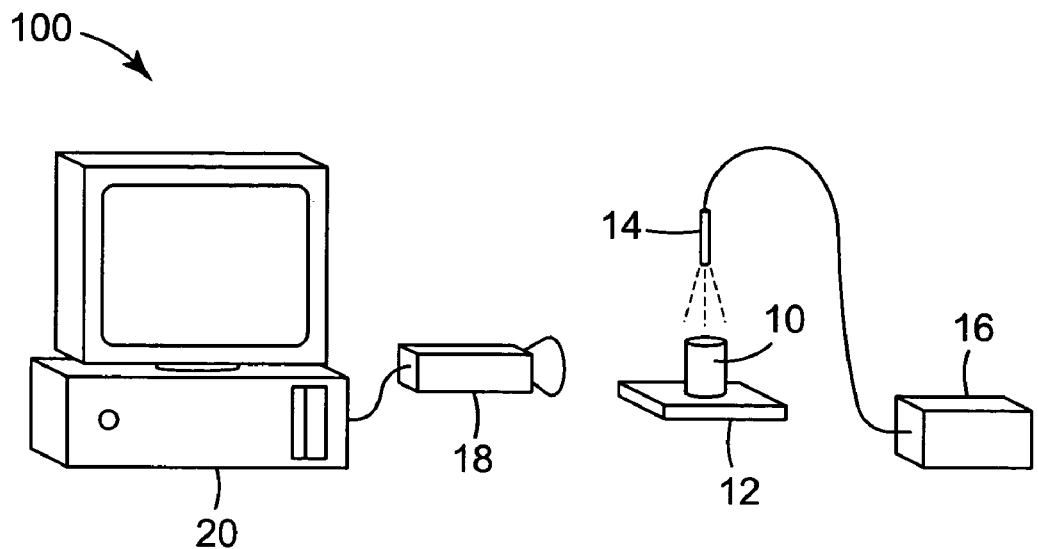
FIG. 1 is a schematic of the apparatus used in the method of the invention.

The method comprises providing a sample of polymerizable monomers, oligomers or crosslinkable polymers, initiating the polymerization, and capturing the thermographic profile of the sample with an IR detector array. A plurality, or an array of samples, may be used with the method of the invention. The samples have a first surface where polymerization may be initiated, and one or more surfaces where the polymerization is monitored and the thermographic profile captured. The "monitoring surfaces" are oriented substantially perpendicular to the initiation surface. By "substantially perpendicular", it is meant that the edges between the initiation surface and a monitoring surface need not be exactly 90°, but may be within ±45°, more preferably within ±25°, most preferably within ±10° of 90°. The choice of the "initiation surface" and the "monitoring surface(s)" may be arbitrary for any particular sample or array of samples, but it is often convenient to initiate polymerization on an upper, horizontal surface, and monitor the polymerization from one of the substantially perpendicular, vertical surfaces.

The samples may be considered to have dimensions along arbitrary x, y and z dimensions. The z dimension may be considered the vertical dimension, and may be considered normal to the plane of a horizontal initiation surface. Generally, the sample size is at least 0.5 mm along the z axis which is normal to the polymerization front; i.e. a hypothetical plane along which polymerization advances through the sample. Preferably the sample size is at least 0.5 mm in depth and 0.1 mm in diameter, i.e. along the x and y axes. While there is no general upper limit, sample sizes are conveniently handled and analyzed if less than 10 cm in depth (z dimension) and 5 cm diameter (x and y dimensions, independently). Within these ranges, adequate information concerning the exothermicity of the polymerization can be captured. However, in some embodiments, it may be useful to monitor and capture the thermographic profile of samples larger than these dimension, as in quality analysis of production articles, such as in the production of large composite panels.

The method of the invention may be used to monitor the polymerization of the requisite monomers, oligomers or polymers to produce thermoplastic, thermoset, elastomeric and thermoplastic elastomeric polymers. As used herein, "polymerizable" refers to functionality directly connected to or indirectly pendant from a monomer, oligomer, and/or polymer backbone (as the case may be) that participates in curing reactions upon exposure to a suitable source of curing energy. Such functionality generally includes not only groups that cure via a free-radical mechanism upon radiation exposure but also groups that cure via a cationic mechanism, an anionic mechanism, a step-growth mechanism, a chain growth mechanism or by a condensation mechanism, and with catalysts or initiators such as a photo- or thermal free-radical initiator, photoacid or photobase generators, or acid or base catalysts. The method may be applied to capturing the thermographic profile of the polymerization of one or more monomers, one or more oligomers, the crosslinking of one or more polymers, or combinations thereof, such as the polymerization of a monomer with an oligomer, or an oligomer with a polymer.

Thermoplastic polymers which may be prepared in the present method include but are not limited to polyolefins and copolymers and blends thereof (including metallocene polyolefins, poly(alpha olefins), and ethylene-propylene-diene terpolymers) styrene copolymers and terpolymers, ionomers, ethylene vinyl acetate, polyvinylbutyrate, polyvinyl chloride, fluorocarbon elastomers, other fluorine-containing polymers, polyester polymers and copolymers, polyamide polymers and copolymers, polyurethanes, polycarbonates, polyketones, and polyureas.

Polyamide polymers that may be prepared include, but are not limited to, synthetic linear polyamides, e.g., nylon-6 and nylon-66, nylon-11, or nylon-12, nylon-612, nylon-69, nylon-4, nylon-42, nylon-46, nylon-7, and nylon-8, ring containing polyamides, e.g., nylon-6T and nylon-6I and polyether containing polyamides, may also be prepared.

Polyurethane polymers which may be prepared include aliphatic, cycloaliphatic, aromatic, and polycyclic polyurethanes. These polyurethanes are typically produced by reaction of a polyfunctional isocyanate with a polyol according to well-known reaction mechanisms.

Other polymers that may be prepared include polyacrylates and polymethacrylates which in general are described by the term (meth)acrylates. Examples include polymers of acrylic acid, methyl acrylate, ethyl acrylate, acrylamide, methacrylic acid, methyl methacrylate, n-butyl acrylate, and ethyl methacrylate. Other polymers that may be prepared include polyesters, polycarbonates, polyketones, and polyureas. Still other polymers include fluorine-containing polymers including polymers and copolymers of tetrafluoroethylene with one or more other monomers such as perfluoro(methyl vinyl) ether, hexafluoropropylene, perfluoro(propyl vinyl)ether; copolymers of tetrafluoroethylene with ethylenically unsaturated hydrocarbon monomers such as ethylene, or propylene.

Still other fluorine-containing polymers that may be prepared include those based on vinylidene fluoride such as polyvinylidene fluoride; copolymers of vinylidene fluoride with one or more other monomers such as hexafluoropropylene, tetrafluoroethylene, ethylene, propylene, etc. Still other useful fluorine-containing extrudable polymers will be known to those skilled in the art as a result of this disclosure.

Polyolefins include the homopolymers and copolymers of olefins, as well as copolymers of one or more olefins copolymerizable with such olefins, e.g., vinyl ester compounds such as vinyl acetate. The olefins have the general structure $CH_2=CHR$, where R is a hydrogen or an alkyl radical, and generally, the alkyl radical contains not more than 10 carbon atoms and preferably one to four carbon atoms. Representative olefins are ethylene, propylene, 1- and 2-butene. Representative monomers which are copolymerizable with these olefins include 1-butene, 1-octene, 1-hexene, 4-methyl-1-pentene, propylene, vinyl ester monomers such as vinyl acetate, vinyl propionate, vinyl butyrate, vinyl chloroacetate, and vinyl chloropropionate; acrylic and alpha-alkyl acrylic acid monomers, and their alkyl esters; amides and nitriles such as acrylic acid, methacrylic acid, ethacrylic acid, methyl acrylate, ethyl acrylate, N,N-dimethyl acrylamide, methacrylamide, acrylonitrile; vinyl aryl monomers such as styrene, o-methoxystyrene, p-methoxystyrene, and vinyl naphthalene; vinyl and vinylidene halide monomers such as vinyl chloride, vinylidene chloride, vinylidene bromide; alkyl ester monomers of maleic and fumaric acid such as dimethyl maleate, diethyl maleate; vinyl alkyl ether monomers such as vinyl methyl ether, vinyl ethyl ether, vinyl isobutyl ether; 2-chloroethyl vinyl ether; and vinyl pyridine monomers.

Thermoset polymers that may be prepared include those derived from phenolic resins, epoxy resins, vinyl ester resins, (meth)acrylate resins, vinyl ether resins, urethane resins, cashew nut shell resins, napthalenic and phenolic resins, epoxy modified phenolic resins, silicone (hydrosilane and hydrolyzable silane) resins, polyimide resins, urea formaldehyde resins, methylene dianiline resins, methylpyrrolidinone resins, acrylate and methacrylate resins, isocyanate resins, unsaturated polyester resins, and mixtures thereof.

Epoxy (epoxide) monomers and prepolymers are commonly used in making thermoset epoxy materials, and are well known in the art. Thermosettable epoxy compounds can be cured or polymerized by cationic polymerization. The epoxy-containing monomer can also contain other epoxy compounds or blends of epoxy containing monomers with thermoplastic materials. The epoxy-containing monomer may be blended with specific materials to enhance the end use or application of the cured, or partially cured, composition.

Epoxy-containing materials include epoxy resins having at least one oxirane ring polymerizable by a ring opening reaction. Such materials, broadly called epoxides, include both monomeric and polymeric epoxides, and can be aliphatic, cycloaliphatic, or aromatic. These materials generally have, on the average, at least two epoxy groups per molecule, and preferably have more than two epoxy groups per molecule. The average number of epoxy groups per molecule is defined herein as the number of epoxy groups in the epoxy-containing material divided by the total number of epoxy molecules present. Polymeric epoxides include linear polymers having terminal epoxy groups (e.g., a diglycidyl ether of a polyoxyalkylene glycol), polymers having skeletal oxirane units (e.g., polybutadiene polyepoxide), and polymers having pendent epoxy groups (e.g., a glycidyl methacrylate polymer or copolymer).

Phenolic resins may also be prepared. Acid cure resole phenolic resins are disclosed in U.S. Pat. No. 4,587,291. Phenolic resins that may be prepared can have a content of monomeric phenols of less than 5% if desired. The resins can also be modified additionally with up to 30% urea, melamine, or furfuryl alcohol, according to known methods.

Phenol resoles are alkaline condensed, reaction products of phenols and aldehydes, wherein either mono- or polynuclear phenols may be used. In further detail, mononuclear phenols, and both mono- and polyfunctional phenols, such as phenol itself, and the alkyl substituted homologs, such as o-, m-, p-cresol or xylenols, are suitable. Also suitable are halogen-substituted phenols, such as chloro- or bromophenol and polyfunctional phenols, such as resorcinol or pyrocatechol. The term "polynuclear phenols" refers, for example, to naphthols, i.e., compounds with fused rings. Polynuclear phenols may also be linked by aliphatic bridges or by heteroatoms, such as oxygen. Polyfunctional, polynuclear phenols may also provide suitable thermosetting phenyl resoles.

The aldehyde component used to form the phenol resoles can be formaldehyde, acetaldehyde, propionaldehyde, or butyraldehyde, or products that release aldehyde under condensation conditions, such as, for example, formaldehyde bisulfite, urotropin, trihydroxymethylene, paraformaldehyde, or paraldehyde. The stoichiometric quantities of phenol and aldehyde components can be in the ratio of 1:1.1 to 1:3.0.

Oxetane ring monomers may also be used to form the matrix phase thermoset polymers. Oxetane (oxacyclobutane) rings behave somewhat like epoxy (oxirane) rings in that catalysts and/or co-curatives, sometimes referred to as crosslinking agents, can be used to open the ring and link two or more chains together to form a crosslinked polymer. For example, polycarboxylic acid anhydrides and other polyfunctional compounds such as polyamines, polycarboxylic acids, polymercaptans, polyacid halides, or the like are capable of linking two or more oxetane sites just as epoxy sites are linked by epoxide co-curatives. The result is an increased amount of three-dimensional structure in the crosslinked or cured polymer, and hence an increased amount of rigidity of the polymer structure.

Thermosettable compositions may include components that have a radiation or heat crosslinkable functionality such that the composition is curable upon exposure to radiant curing energy in order to cure and solidify, i.e. polymerize and/or crosslink, the composition, and which may be monitored by the method of the invention. Representative examples of radiant curing energy include actinic energy (e.g., infrared energy, microwave energy, visible light, ultraviolet light, and the like), accelerated particles (e.g., electron beam energy), and/or energy from electrical discharges (e.g., coronas, plasmas, glow discharge, or silent discharge).

Radiation crosslinkable functionality refers to functional groups directly or indirectly pendant from a monomer, oligomer, or polymer backbone that participate in crosslinking and/or polymerization reactions upon exposure to a suitable source of radiant curing energy. Representative examples of radiation crosslinkable groups suitable in the practice of the present invention include epoxy groups, (meth)acrylate groups, olefinic carbon-carbon double bonds, triple bonds, allylether groups, styrene groups, (meth)acrylamide groups, combinations of these, and the like.

Thermosetting polymeric elastomers that may be prepared include those derived from crosslinked polyurethanes, crosslinked acrylates, crosslinked natural rubber, crosslinked synthetic rubbers, crosslinked epichlorohydrin, crosslinked chlorosulfonated polyethylene, crosslinked ethylene-acrylic, acrylonitrile-butadiene (NBR), butadiene rubber, chlorinated and chlorosulfonated polyethylene, chloroprene, EPM, EPDM, epichlorohydrin, isobutylene-isoprene, isoprene, polysulfide, polyurethane, silicone, PVC-NBR, styrene-butadiene, and vinyl acetate-ethylene and the like.

The method of the invention is also useful in the polymerization of materials to produce interpenetrating polymer networks (IPN) and semi-IPNs. An IPN results when two polymers are formed in the presence of each other and result in two independent crosslinked polymer networks. IPNs wherein one of the polymers is an epoxy resin have been described. IPNs have been prepared by polymerizing free-radically polymerizable ethylenically-unsaturated acrylate-type monomers and epoxy monomers simultaneously or sequentially. See, for example, U.S. Pat. Nos. 5,399,637, 5,376,428, 5,086,086 and 4,952,612.

Semi-interpenetrating polymer networks (semi-IPNs) are defined as polymer networks of two or more polymers wherein one polymer is crosslinked and one is uncrosslinked. Semi-IPNs comprising a number of polymeric systems have been described (Encyclopedia of Polymer Science and Engineering Vol. 8; John Wiley & Sons, New York (1984) p. 279-332. Semi-IPNs comprising uncured epoxy resins as the major constituent and, as minor constituents, butadiene-acrylonitrile rubber (G.B. Patent No. 736,457), a crosslinked elastomeric latex (G.B. Patent No. 1,247,116) have been described. Semi-interpenetrating polymer networks of polyolefins and tri-epoxy resins have been studied by Negmatov et at., Uzb. Khim. Zh., 1990 (6), 65-7; CA 115:93689n (1991). No curatives, amounts of components, or processes of making the IPN are disclosed.

Representative examples of photopolymerizable groups suitable in the practice of the present invention include epoxy groups, (meth)acrylate groups, olefinic carbon-carbon double bonds, allyloxy groups, alpha-methyl styrene groups, (meth)acrylamide groups, cyanate ester groups, vinyl ethers groups, combinations of these, and the like.

One useful class of photopolymerizable materials is thiol-ene polymers comprising at least one monomer having one or more ethylenically unsaturated groups, at least one polythiol; and a free radical polymerization photoinitiator, or blend of photoinitiators, with absorption in the UV and/or visible range sufficient to initiate photopolymerization. Typically these photoinitators and their mixtures may contain ketone functionality and are also useful in the free radical photopolymerization of acrylates. The photoinitators can broadly be classified as acetophenone type of photoinitiators, acyl phosphine oxide type of initiators or benzophenone type of photoinitators. Further, any of the aforementioned categories can have synergists such as electron donating compounds and dye sensitizers. A list of photoinitiators is incorporated herein by reference to K. Dietliker in "A Compilation of Photoinitiators Commercially Available for UV Today", SITA Technology (2002) and J. V. Crivello and K. Dietliker in Chemistry and Technology of UV & EB Formulations for Coatings, Inks and Paints, Vol. III, SITA Technology (1998).

Particularly useful examples of ethylenically unsaturated vinyl monomers or oligomers include: styrene, alkylstyrenes, halostyrenes, acrylonitrile, vinyl chloride, vinylidene chloride; vinyl ethers, such as 1,4-cyclohexanedimethanol divinyl ether (CHVE) and diethyleneglycol divinyl ether (DVE); vinyl esters, such as vinyl acetate; and N-vinyl derivatives, such as N-vinylpyrrolidone and N-vinyl formamide.

Useful examples of ethylenically unsaturated acrylic monomers or oligomers include: alkyl or hydroxyalkyl(meth)

acrylates such as methyl(meth)acrylate, ethyl(meth)acrylate, butyl(meth)acrylate, (meth)acrylamide, 2-ethylhexylacrylate, 2-hydroxyethyl acrylate, isobornyl acrylate, glycerol diacrylate, glycerol triacrylate, tetraethylene glycol diacrylate, 1,4-butanediol diacrylate, ethylene glycol diacrylate, diethylene glycol diacrylate, triethylene glycol dimethacrylate, 1,6-hexanediol diacrylate, 1,3-propanediol diacrylate, 1,3-propanediol dimethacrylate, trimethylolpropane triacrylate, 1,2,4-butanetriol trimethylacrylate, 1,4-cyclohexanediol diacrylate, pentaerythritol triacrylate, pentaerythritol tetraacrylate, pentaerythritol tetramethacrylate, sorbitol hexacrylate, bis[1-(2-acryloxy)]-p-ethoxyphenyl dimethylmethane, bis[1-(3-acryloxy-2-hydroxy)]-p-propoxyphenyldimethylmethane, tris(hydroxyethyl)isocyanurate trimethacrylate, epoxy acrylates, urethane acrylates, and ethoxylated acrylates. Particularly useful highly functional acrylates are, for example, trimethylolpropane triacrylate (TMPTA), trimethylolpropane ethoxy triacrylate, and pentaerythritol triacrylate (PETA). Blends of acrylates can be made to adjust cure rate and final properties of the cured material.

Useful examples of compounds having a plurality of thiol groups (polythiols) include ethylene glycol bis(thioglycolate), ethylene glycol bis(β-mercaptopropionate), trimethylolpropane tris(thioglycolate), trimethylolpropane tris(mercaptopropionate), pentaerythritol tetrakis(thioglycolate) and pentaerythritol tetrakis(β-mercaptopropionate), all of which are commercially available. A specific example of a preferred polymeric polythiol is polypropylene ether glycol bis(β-mercaptopropionate) which is prepared from polypropyleneether glycol (e.g. Pluracol P201, BASF Wyandotte Chemical Corp.) and b-mercaptopropionic acid by esterification. Poly-α-mercaptoacetate or poly-β-mercaptopropionate esters, particularly the trimethylolpropane triesters or pentaerythritol tetraesters are preferred. Other polythiols which may be suitably employed include alkyl thiol functional compounds such as 1,2-dimercaptoethane, 1,6-dimercaptohexane and the like. Thiol terminated polysulfide resins may also be employed. Particularly useful highly functional polythiols include pentaerythritol tetramercaptopropionate and trimethylolpropane mercaptopropionate.

Useful light curing photoinitiators for polymerization of thiol-ene samples include acetophenone derivatives, acyl phosphine oxides or acyl phosphine oxides blended with commercially available initiators that are capable of free radical initiation at a wavelength greater than 250 nanometers with or without synergists such as electron donating compounds or dye sensitizers.

Photopolymerizations are initiated by exposure of the sample to a source of actinic radiation, such as UV radiation. In the method of the invention, the wavelength, intensity and area of irradiation may be varied to determine the effect on the polymerization. In many cases it may be advantageous to restrict the area of irradiation to some portion of a surface to avoid scattering effects of the light source and consequent multiple points of initiation. Thus the source of irradiation or the aperture of the source may be constrained to a portion of a first surface of a sample, and the thermographic profile of a second surface captured, so that polymerization is not initiated at the second surface.

Polymerizations may be studied using photoinitiators that are reactive to any source of actinic radiation, including UV or visible light. A visible light source may be used since it is more convenient and is considered less hazardous. Samples may be screened at a given intensity, rate and duration of radiation so that it will advance the polymerization at a reasonable rate without deleteriously affecting the polymer segment being produced, to maximize the physical properties, or to determine the optimum reaction conditions, for example.

For free radical polymerization (hardening), an initiation system can be selected from systems that initiate polymerization via radiation, heat, or redox/auto-cure chemical reaction. A class of initiators capable of initiating polymerization of free radically active functional groups includes free radical-generating photoinitiators, optionally combined with a photosensitizer or accelerator. Such initiators typically can be capable of generating free radicals for addition polymerization upon exposure to light energy having a wavelength between 200 and 800 nm.

A variety of visible or near-IR photoinitiator systems may be used for photopolymerization of free-radically polymerizable resin. For example, a photoinitiation system can be selected from systems which initiate polymerization via a two component system of an amine and an α-diketone as described in U.S. Pat. No. 4,071,424. Alternatively, the resin can be combined with a three-component photoinitiator system such as described in U.S. Pat. No. 5,545,676 (Palazzotto et al.). The three-component system includes an iodonium salt (i.e., a diaryliodonium salt), a sensitizer, and a donor. Each photoinitiator component is discussed in U.S. Pat. No. 5,545,676, column 2, line 27, to column 4, line 45. Other useful free-radical initiators include the class of acylphosphine oxides, as described in European Pat. Application No. 173567, U.S. Pat. No. 4,737,593 and United Kingdom Patent No. GB 2,310,855.

Tertiary amine reducing agents may be used in combination with an acylphosphine oxide. Illustrative tertiary amines useful in the invention include ethyl 4-(N,N-dimethylamino) benzoate and N,N-dimethylaminoethyl methacrylate. The initiator can be used in catalytically-effective amounts, based on the weight of ethylenically-unsaturated compound present, of the acylphosphine oxide plus from 0.1 to 5 weight percent, based on the weight of ethylenically-unsaturated compound present, of the tertiary amine.

Another free-radical initiator system that can alternatively be used in the dental materials of the invention includes the class of ionic dye-counterion complex initiators comprising a borate anion and a complementary cationic dye. Borate salt photoinitiators are described, for example, in U.S. Pat. Nos. 4,772,530, 4,954,414, 4,874,450, 5,055,372, and 5,057,393.

Yet another alternative class of initiators capable of initiating polymerization of free radically active functional groups in the hardenable resin includes conventional chemical initiator systems such as a combination of a peroxide and an amine. These initiators, which rely upon a thermal redox reaction, are often referred to as "auto-cure catalysts." They are typically supplied as two-part systems in which the reactants are stored apart from each other and then combined immediately prior to use.

Useful photoinitiators include benzoin ethers (such as benzoin methyl ether or benzoin isopropyl ether), substituted benzoin ethers (such as anisoin methyl ether), substituted acetophenones (such as 2,2-diethoxyaceto-phenone and 2,2-dimethoxy-2-phenylacetophenone), substituted alpha-ketols (such as 2-methyl-2-hydroxypropiophenone), aromatic sulfonyl chlorides (such as 2-naphthalenesulfonyl chloride) and photoactive oximes. Examples of commercially available photoinitiators include Irgacure™ 819 and Darocur™ 1173 (both available form Ciba-Geigy Corp., Hawthorne, N.Y.), Lucern TPO™ (available from BASF, Parsippany, N.J.) and Irgacure™ 651, (2,2-dimethoxy-1,2-diphenyl-1-ethanone) available from Ciba-Geigy.

Photoinitiators may often be used with a sensitizer. The effect of various sensitizers and concentrations thereof on polymerization compositions may be determined using the method of the invention. Suitable sensitizers are believed to include compounds in the following categories: ketones, coumarin dyes (e.g., ketocoumarins), xanthene dyes, acridine dyes, thiazole dyes, thiazine dyes, oxazine dyes, azine dyes, aminoketone dyes, porphyrins, aromatic polycyclic hydrocarbons, p-substituted aminostyryl ketone compounds, aminotriaryl methanes, merocyanines, squarylium dyes and pyridinium dyes. Ketones (e.g., monoketones or alpha-diketones), ketocoumarins, aminoarylketones and p-substituted aminostyryl ketone compounds are preferred sensitizers. For applications requiring deep cure (e.g., cure of highly-filled composites), one may employ sensitizers having an extinction coefficient below about 1000 L mol$^{-1}$ cm$^{-1}$, more preferably about or below 100 L mol$^{-1}$ cm$^{-1}$, at the desired wavelength of irradiation for photopolymerization.

If the energy source is ultraviolet radiation, a suitable ultraviolet light transparent vessel may be used to contain the sample. UV light sources can be of two types: 1) relatively low light intensity sources such as blacklights which provide generally 10 mW/cm$^2$ or less (as measured in accordance with procedures approved by the United States National Institute of Standards and Technology as, for example, with a UVIMA™ UM 365 L-S radiometer manufactured by Electronic Instrumentation & Technology, Inc., in Sterling, Va.) over a wavelength range of 280 to 400 nanometers and 2) relatively high light intensity sources such as medium pressure mercury lamps which provide intensities greater than 10 mW/cm$^2$, generally between 15 and 5000 mW/cm$^2$. The intensity and the exposure times may be varied to investigate either fully- or partially cured polymer compositions, as well as the effect of various monomers, catalysts, and amounts thereof. Intensities can range from about 0.1 to about 150 mW/cm$^2$, for example from about 0.5 to about 100 mW/cm$^2$, or from about 0.5 to about 50 mW/cm$^2$. Times may vary from as little as a second, to several minutes or more. Ideally, samples may be screened to approximate cure conditions of the desired end-use. If actinic radiation extends beyond 400 nanometers, other light sources including quartz tungsten halogen lamps, tungsten lamps, mercury arcs, carbon arcs, light emitting diodes, lasers and microwave driven electrodeless lamps with or without dopants.

If desired, filters may be used to reduce or eliminate the IR component of the radiation source, and increase the signal to noise ratio (S/N) of the captured thermographic profile. So-called cut-off filters are of generally three types; water filters which are placed between the source and the sample, absorptive filters which are used for low intensity UV sources and are also placed between the source and sample, and reflective filters, which reflect the IR component, but transmit other wavelengths or transmit IR and reflect the visible.

Other optical components such as lenses or diffuser plates may be used to ensure uniformity of actinic radiation. Alternatively, optical components may be used to provide an actinic radiation gradient (intensity gradient) across the sample(s).

Thermally polymerizable samples may be initiated by contact of the sample with a heat source. In one embodiment, the sample(s) may be mounted on or in contact with a heated container, or the sample may be in contact with a heated sample stage, such as a programmable hotplate. Alternatively, the samples may be contained within a heated chamber having an IR transmissive window, such as a quartz window, for capture of the thermographic profile. If desired the samples may be exposed to a thermal gradient by use of a gradiant heat source. The thermographic profile of the apparatus may be captured and subtracted from that of the polymerizable sample. Preferably, a "blank" sample comprising the composition of interest, but lacking an initiator, is subjected to the reaction conditions, the thermographic profile captured, and then compared with the polymerizable sample. This provides an indication of the degree of absorptive heating as opposed to the heat generated by the reaction.

Examples of suitable thermal initiators include peroxides such as benzoyl peroxide, dibenzoyl peroxide, dilauryl peroxide, cyclohexane peroxide, methyl ethyl ketone peroxide, hydroperoxides, e.g., tert-butyl hydroperoxide and cumene hydroperoxide, dicyclohexyl peroxydicarbonate, 2,2,-azo-bis(isobutyronitrile), and t-butyl perbenzoate. Examples of commercially available thermal initiators include initiators available from DuPont Specialty Chemical (Wilmington, Del.) under the VAZO trade designation including VAZO™ 64 (2,2'-azo-bis(isobutyronitrile)), VAZO™ 67 (2,2'-Azobis (2-methylbutyronitrile)), and VAZO™ 52, and Lucidol™ 70 from Elf Atochem North America, Philadelphia, Pa.

Cationically polymerizably samples may be polymerized with acid generating initiators such as photoacid generators or thermal acid generators. Useful photoacid generators include ionic photoacid generators, including onium salts and organometallic salts, such as iron arene complexes; and non-ionic photoacid generators, including organosilanes, latent sulfonic acids and other miscellaneous non-ionic compounds, such as halomethyl triazines (such as those described in U.S. Pat. No. 3,987,037, incorporated herein by reference) and chlorinated acetophenones. Photoacid generators are known and reference may be made to J. V. Crivello and K. Dietliker, Chemistry and Technology of UV and EB Formulation for Coatings, Inks and Paints, vol. III, SITA Technology Ltd., London, 1998. Further reference may be made to Kirk-Othmer Encyclopedia of Chemical Technology, 4th Edition, Supplement Volume, John Wiley and Sons, New York, pp. 253-255.

Useful onium salts include diazonium salts, such as aryl diazonium salts; halonium salts, such as diarlyiodonium salts; sulfonium salts, such as triarylsulfonium salts (including the commercially available UVI 6976™, available from Dow Chemical, Danbury, Conn.); selenonium salts, such as triarylselenonium salts; sulfoxonium salts, such as triarylsulfoxonium salts; and other miscellaneous classes of onium salts such as triaryl phosphonium and arsonium salts, and pyrylium and thiopyrylium salts. Useful organosilanes include mixtures of silanols and aluminum (III) complexes of β-keto esters or β-diketones; o-nitrobenzyl triarylsilyl ethers; triarylsilyl peroxides; and acylsilanes. Useful latent sulfonic acids include α-sulfonyloxy ketones; α-hydroxymethylbenzoin sulfonates; o-nitrobenzyl esters of sulfonic acids; aryl diazidonapthaquinone-4-sulfonates; α-sulfonyl acetophenones; methanesulfonate esters of 2-hydroxy and 2,4-dihydroxybenzophenone (in the presence of thiols); sulfonated N-hydroxy amides or imides; and iminosulfonates. Ternary photoinitiator systems are also efficient in generating photoacid. See Oxman et al U.S. Pat. No. 6,025,406.

Useful thermal acid generators include any polymeric or non-polymeric compounds that release one or more molecules of acid on exposure to thermal energy. Useful thermal acid generators have an activation temperature of less than the decomposition temperature of the vinyl alcohol polymer and generally have an activation temperature of 200° C. or less, preferably 170° C. or less. Additionally, the thermal acid generator should have an activation temperature at least 20° C. above the melt temperature of the donor layer, if coated from the melt. As used herein, "activation temperature" is that temperature at which the thermal release of the incipient acid by the thermal acid generator in the donor layer occurs. Typically the thermal acid generator will have an activation temperature from about 50° C. to about 170° C.

One useful class of thermal acid initiators includes polymeric or non-polymeric halotriazines. Halogenated triazine compounds substituted by at least one trihalomethyl group are disclosed for example in U.S. Pat. No. 4,505,793 and in U.S. Pat. No. 3,987,037, incorporated herein by reference.

Dental materials represent particular challenges in the selection or materials and curing thereof. Unlike other applications, dental materials are often cured in contact with biological materials including the patient's dental enamel, dentin and gums. Useful dental materials must have high strength and durability, must be easily molded and cure (harden) quickly. Unfortunately high cure rates could expose a patient to unacceptably high temperatures, so dental materials must be screened for rapid, complete cure to sufficient hardness, but not exceed temperatures, or durations of temperatures that would cause discomfort to a patient. It has been reported that a 5° C. rise in pulp temperature causes necrosis of a tooth 15% of the time, a 10° C.>60% of the time and a 15° C., 100% of the time (Leo Zach and Gerson Cohen, Endodontics, pg 515, 1965). Generally the exotherms of dental materials that are cured in the oral cavity are such that the temperature rise of the dental pulp is less than 5° C., preferably less than 2.5° C. The present method allows samples to be rapidly screened for such exotherms, using samples that may simulate the size and shape of dental prosthetic materials.

Using the method of the invention, one or more samples can be quickly and reliably screened for suitability in dental applications. In particular, the captured thermographic profile can provide information about the onset of polymerization, the peak temperature achieved, and the rate of heat loss from a sample. The samples may be sized to approximate that of a particular dental prosthetic. Further, samples may be screened by varying the component monomers, other additives (such as reinforcing fillers) and amounts thereof, initiator and amounts thereof, wavelength of exposed radiation, and duration thereof.

Dental materials, whether used for dental sealants, dental adhesives, dental cements, restoratives or prosthetics generally comprise a curable resin, a filler and an initiator.

Dental resins are thermosetting resins capable of being hardened to form a polymer network. Suitable resins include acrylate resins, methacrylate resins, epoxy resins, vinyl resins, and mixtures thereof. Preferably, the hardenable resin is made from one or more matrix-forming oligomer, monomer, or polymer, or blends thereof.

For dental composites, suitable polymerizable resins include hardenable organic resins having sufficient strength, hydrolytic stability, and non-toxicity to render them suitable for use in the oral environment. Examples of such resins include acrylate, methacrylate, urethane, carbamoylisocyanurate, epoxy resins, and mixtures and derivatives thereof. U.S. Pat. Nos. 3,066,112, 3,539,533, 3,629,187, 3,709,866, 3,751,399, 3,766,132, 3,860,556, 4,002,669, 4,115,346, 4,259,117, 4,292,029, 4,308,190, 4,327,014, 4,379,695, 4,387,240 and 4,404,150 disclose such resins.

One class of hardenable resins are materials having free radically active functional groups and include monomers, oligomers, and polymers having one or more ethylenically unsaturated groups. Alternatively, the hardenable resin can be a material from the class of resins that include cationically active functional groups. In another alternative, a mixture of hardenable resins that include both cationically curable and free radically curable resins may be used.

In the class of hardenable resins having free radically active functional groups, suitable materials for use in the invention contain at least one ethylenically unsaturated bond, and are capable of undergoing addition polymerization. Such free radically polymerizable materials include mono-, di- or polyacrylates and methacrylates such as methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, the diglycidyl methacrylate of bisphenol A ("Bis-GMA"), bis[1-(2-acryloxy)]-p-ethoxyphenyldimethylmethane, bis[1-(3-acryloxy-2-hydroxy)]-p-propoxyphenyldimethylmethane, and trishydroxyethyl-isocyanurate trimethacrylate; the bis-acrylates and bis-methacrylates of polyethylene glycols of molecular weight 200 to 500, copolymerizable mixtures of acrylated monomers such as those in U.S. Pat. No. 4,652,274, and acrylated oligomers such as those of U.S. Pat. No. 4,642,126; and vinyl compounds such as styrene, diallyl phthalate, divinyl succinate, divinyl adipate and divinylphthalate. Mixtures of two or more of these free radically polymerizable materials can be used if desired.

For free radical polymerization (hardening), an initiation system can be selected from systems that initiate polymerization via radiation, heat, or redox/auto-cure chemical reaction. A class of initiators capable of initiating polymerization of free radically active functional groups includes free radical-generating photoinitiators, optionally combined with a photosensitizer or accelerator. Such initiators typically can be capable of generating free radicals for addition polymerization upon exposure to light energy having a wavelength between 200 and 800 nm.

A variety of visible or near-IR photoinitiator systems may be used for photopolymerization of free-radically polymerizable resin. For example, a photoinitiation system can be selected from systems which initiate polymerization via a two component system of an amine and an α-diketone as described in U.S. Pat. No. 4,071,424. Alternatively, the resin can be combined with a three-component photoinitiator system such as described in U.S. Pat. No. 5,545,676 (Palazzotto et al.). The three-component system includes an iodonium salt (i.e., a diaryliodonium salt), a sensitizer, and a donor. Each photoinitiator component is discussed in U.S. Pat. No. 5,545,676, column 2, line 27, to column 4, line 45. Other useful free-radical initiators include the class of acylphosphine oxides, as described in European Pat. Application No. 173,567, U.S. Pat. No. 4,737,593 and United Kingdom Patent No. GB 2,310,855.

Tertiary amine reducing agents may be used in combination with an acylphosphine oxide. Illustrative tertiary amines useful in the invention include ethyl 4-(N,N-dimethylamino) benzoate and N,N-dimethylaminoethyl methacrylate. The initiator can be used in catalytically-effective amounts, based on the weight of ethylenically-unsaturated compound present, of the acylphosphine oxide plus from 0.1 to 5 weight percent, based on the weight of ethylenically-unsaturated compound present, of the tertiary amine.

Another free-radical initiator system that can alternatively be used in the dental materials of the invention includes the class of ionic dye-counterion complex initiators comprising a borate anion and a complementary cationic dye. Borate salt photoinitiators are described, for example, in U.S. Pat. Nos. 4,772,530, 4,954,414, 4,874,450, 5,055,372, and 5,057,393.

Yet another alternative class of initiators capable of initiating polymerization of free radically active functional groups in the hardenable resin includes conventional chemical initiator systems such as a combination of a peroxide and an amine. These initiators, which rely upon a thermal redox reaction, are often referred to as "auto-cure catalysts." They are typically supplied as two-part systems in which the reactants are stored apart from each other and then combined immediately prior to use.

In a further alternative, heat may be used to initiate the hardening, or polymerization, of free radically active groups. Examples of heat sources suitable for the dental materials of the invention include inductive, convective, and radiant. Thermal sources should be capable of generating temperatures of at least 40° C. to 150° C. under normal conditions or at elevated pressure. This procedure is preferred for initiating polymerization of materials occurring outside of the oral environment.

Yet another alternative class of initiators capable of initiating polymerization of free radically active functional groups in the hardenable resin are those that include free radical-generating thermal initiators. Examples include peroxides such as, e.g., benzoyl peroxide and lauryl peroxide, and azo compounds such as, for example, 2,2-azobis-isobutyronitrile (AIBN).

Now returning to the hardenable resins, an alternative class of hardenable resins useful in the inventive material includes cationically active functional groups. Materials having cationically active functional groups include cationically polymerizable epoxy resins, vinyl ethers, oxetanes, spiro-orthocarbonates, spiro-orthoesters, and the like.

Preferred materials having cationically active functional groups are epoxy resins such as those disclosed in U.S. Pat. No. 6,025,406 (Oxman et al.) at column 2, line 36, to column 4, line 52. Optionally, monohydroxy- and polyhydroxy-alcohols may be added to the hardenable resin, as chain-extenders for the epoxy resin. The hydroxyl-containing material used in the present invention can be any organic material having hydroxyl functionality of at least 1, and preferably at least 2.

For hardening resins comprising cationically active functional groups, an initiation system can be selected from systems that initiate polymerization via radiation, heat, or redox/auto-cure chemical reaction. For example, epoxy polymerization may be accomplished by the use of thermal curing agents, such as anhydrides or amines. A particularly useful example of an anhydride curing agent would be cis-1,2-cyclohexanedicarboxylic anhydride. Alternatively and preferably, initiation systems for resins comprising cationically active functional groups are those that are photoactivated. The broad class of cationic photoactive groups recognized in the catalyst and photoinitiator industries may be used in the practice of the present invention. Photoactive cationic moieties, and photoactive cationic organic compounds are art recognized classes of materials as exemplified by U.S. Pat. Nos. 4,250,311; 3,708,296; 4,069,055; 4,216,288; 5,084,586; 5,124,417; 4,985,340, 5,089,536, and 5,856,373. The cationically-curable materials can be combined with a three component or ternary photoinitiator system, as described above.

For hardening cationically curable resins, examples of useful aromatic iodonium complex salts are disclosed in U.S. Pat. No. 6,025,406, column 5, line 46, to column 6, line 9. Examples of useful sensitizers and electron donors can also be found in U.S. Pat. No. 6,025,406, column 6, line 43, to column 9, line 43, incorporated herein by reference. An alternative photoinitiator system for cationic polymerizations includes the use of organometallic complex cations essentially free of metal hydride or metal alkyl functionality selected from those described in U.S. Pat. No. 4,985,340. Organometallic salts are known in the art and can be prepared as described in, for example, EPO No. 094,914 and U.S. Pat. Nos. 5,089,536, 4,868,288, and 5,073,476.

The samples, particularly when screening for dental composites, can also contain fillers. Fillers may be selected from one or more of a wide variety of materials suitable for incorporation in compositions used for medical (e.g., dental) applications, such as fillers currently used in dental restorative compositions, and the like. The filler is preferably finely divided. The filler can have a unimodial or polymodial (e.g., bimodal) particle size distribution. Preferably, the maximum particle size (the largest dimension of a particle, typically, the diameter) of the filler is less than about 10 micrometers, and more preferably less than about 2.0 micrometers. Preferably, the average particle size of the filler is less than about 3.0 micrometers, and more preferably less than about 0.6 micrometer.

The filler can be an inorganic material. It can also be a crosslinked organic material that is insoluble in the resin system, and is optionally filled with inorganic filler. The filler should in any event be nontoxic and suitable for use in the mouth. The filler can be radiopaque or radiolucent. The filler is also substantially insoluble in water.

Examples of suitable inorganic fillers are naturally occurring or synthetic materials including, but not limited to: quartz; nitrides (e.g., silicon nitride); glasses derived from, for example, Ce, Sb, Sn, Ba, Zn, and Al; feldspar; borosilicate glass; kaolin; talc; titania; low Mohs hardness fillers such as those described in U.S. Pat. No. 4,695,251 (Randklev); and colloidal and submicron silica particles (e.g., pyrogenic silicas such as those available under the trade designations AEROSIL, including "OX 50", "130", "150" and "200" silicas from Degussa Corp., Akron, Ohio and CAB-O-SIL M5 silica from Cabot Corp., Tuscola, Ill.). Examples of suitable organic filler particles include filled or unfilled pulverized polycarbonates, polyepoxides, and the like.

The filler can also be an acid-reactive filler. An acid-reactive filler is typically used in combination with an acid-functional resin component, and may or may not be used in combination with a nonreactive filler. The acid-reactive filler can, if desired, also possess the property of releasing fluoride. Suitable acid-reactive fillers include metal oxides, glasses, and metal salts. Preferred metal oxides include barium oxide, calcium oxide, magnesium oxide, and zinc oxide. Preferred glasses include borate glasses, phosphate glasses, and fluoroaluminosilicate ("FAS") glasses. FAS glasses are particularly preferred. The FAS glass preferably contains sufficient elutable cations so that a hardened dental composition will form when the glass is mixed with the components of the hardenable composition. The glass also preferably contains sufficient elutable fluoride ions so that the hardened composition will have cariostatic properties. The glass can be made from a melt containing fluoride, alumina, and other glass-forming ingredients using techniques familiar to those skilled in the FAS glassmaking art. The FAS glass preferably is in the form of particles that are sufficiently finely divided so that they can conveniently be mixed with the other cement components and will perform well when the resulting mixture is used in the mouth.

The filler is added in amounts sufficient to provide a hardenable composition having desirable mixing and handling properties before hardening, and good performance after hardening. Generally, the filler represents no greater than about 90 wt-%, more preferably no greater than about 85 wt-%, and most preferably no greater than about 80 wt-%, of the total weight (including water) of the hardenable composition components. Preferably, the filler represents at least about 1 wt-%, more preferably at least about 5 wt-%, and most preferably at least about 30 wt-%, of the total weight (including water) of the hardenable composition components, but may be varied as desired by the method of the invention.

The thermographic image of the sample(s) may be captured with an IR detector array, which may comprise an infrared pyrometer array (i.e. two or more IR pyrometers), an infrared camera, and preferably a digital infrared camera. The detectors should have a useful temperature range of from about −20° C. to about 250° C., preferably from about 20° C. to about 200° C. The detectors should further have a temperature resolution of ±0.5° C., preferably ±0.1° C. and most preferably ±0.02° C. One or more detectors may be used.

Pyrometers are non-contact temperature sensors that measure temperature from the amount of thermal electromagnetic radiation received from a spot on the sample. This group of sensors includes both spot or "point" measuring devices in addition to line measuring radiation thermometers, which produce 1-D and, with known relative motion, can produce 2-D temperature distributions, and thermal imaging, or area measuring, thermometers which measure over an area from which the resulting image can be displayed as a 2-D temperature map of the region viewed. IR optical pyrometers are sensitive to infrared wavelengths and typically convert the input wavelength to an optical or electronic output by means of an IC, resistance temperature detector or thermocouple. In this context, infrared optical pyrometers are not to be confused with other optical pyrometers that measure temperatures of very hot objects (>700° C.) based upon their visible light emission due to incandescence. Useful IR pyrometers will measure infrared output between 6-14 micrometers in the IR and generally have a useful temperature range of −20 to 538° C.; well beyond that required for measuring the exothermicity of polymerizations using the method of the invention. One useful IR pyrometer is an Omega Industrial IR thermometer (OS552-V1-6).

The majority of devices in use are single waveband thermometers (they measure a portion of the received thermal radiation in a single waveband, or portion of the infrared part of the electromagnetic spectrum). However, the number of ratio thermometers (two color pyrometers) on the market has grown considerably. Single waveband radiation thermometers are usually against a blackbody source in order to provide accurate surface temperature measurements.

An infrared camera may be a line-scan camera in which a linear array of sensors is translated across the focal plane of the camera to produce a two-dimensional image, or it can contain a two-dimensional array of sensors. Linear arrays may be 120 pixels or more, while two-dimensional arrays are commonly 120 pixels×120 pixels, 256 pixels×256 pixels, 240 pixels×320 pixels or sometimes more.

The sensor elements can be microbolometers, in which the infrared radiation impinging on a micro-machined pad alters the resistance of a circuit, a thermoelectric sensor in which the micro-machined pad contains the hot electrode of a thermocouple, or a pyroelectric sensor in which radiative heating of the pad causes a change in capacitance. Thermal sensors of these kinds are usually sensitive to infrared light in the long wavelength range of 8-14 micrometers, although pyroelectric sensors may be used across a much wider range of wavelengths, even into the near IR. Alternatively, the sensor element may be a photoelectric material such as indium antimonide (InSb), mercury cadmium telluride (MCT), platinum silicide (PtSi), lead selenide (PbSe) and others, which are generally used to detect infrared radiation between 3 and 5 micrometers. Gallium arsenide (GaAs) has also been used to create an IR detector array sensitive to 0.9-1.7 micrometers. A third type of sensor element is the quantum well infrared photodetector (QWIP) that operates at wavelengths of 8-9 micrometers. It should be noted that thermal sensors may be operated at room temperature, unlike photoelectric sensors and QWIPs that are usually cooled to near liquid nitrogen temperatures to achieve the optimal sensitivity. Some photometric sensors (e.g.: PbSe) that are designed to be sensitive to the near-IR may be operated at ambient temperatures. Cameras may also be radiometric, in which they are calibrated against a blackbody and thus able to give the real surface temperature of an object (assuming various parameters such as emissivity, distance etc. are known) or not. The thermal sensitivity varies with sensor type and manufacturer, but is generally on the order of 20 mK (InSb, MCT, QWIP) or higher. The thermal sensitivity, or NETD, varies.

In principle, blackbody radiation is emitted at shorter wavelengths as the emitting body gets hotter and thus cameras sensitive to shorter wavelengths are more commonly used for hotter bodies. However, the optimal camera for any given application will be a function of sensitivity, image stability, measured temperature range, desired image resolution (number of pixels), frame rate, and emissivities and transparencies of anticipated materials in the relevant wavelength range, as well as reliability and cost.

Typical commercial cameras are available from vendors such as FLIR Systems, Electrophysics Corp., Infrared Solutions, Inc., CMC Electronics, Mikron and others. Note that not all IR cameras are video cameras, some only record still images. The output signal can displayed on a screen on the camera, saved to memory (onboard RAM or an ancillary memory device), provided to a personal computer through a Firewire™, frame-grabber interface, or for higher frame rates or larger arrays it can be communicated through a high speed interface to a dedicated computer, such as is available from Dolch Computer Systems.

Since IR images are commonly output as 12- or 14-bit data files, many commercial image-handling packages are not applicable. Consequently cameras generally come with their own manufacturer's proprietary software packages. Standard features include the ability to subtract one image from another, or from a string of images to create a "normalized" video, identification of maximum and minimum temperatures within an image (or a defined region or line), the ability to track the temperature of a given pixel through a sequence of images (a video) generating a time/temperature profile, a variety of false color palettes, and many other functions. Thus the software allows one to map a selected sample area, and to plot the data as a function of time.

The IR detector array is normally oriented substantially perpendicular to the surface of initiation ("initiation surface") of the polymer sample; that is, if the sample is initiated on a first surface, the IR detector is oriented to monitor a second surface substantially perpendicular to the first surface. Optionally thermographic profile of additional surfaces can also be captured. Multiple points on surfaces other than the initiation surface are typically monitored. The array may monitor one or more points on a single surface other than the initiation surface, or one or more points on separate surfaces other than the initiation surface. It will be understood that the samples may have surfaces that are not mutually perpendicular, but the method of the invention may still be applied. For example, wedge-shaped samples may be used advantageously as described with reference to FIG. 2. Additionally, one or more points on two or more samples may be monitored and the thermographic profile captured.

The points which are monitored, and which result in the thermographic profile, may vary considerable in size depending on the resolution of the IR detector used, and the distance of the detector from the sample(s). Infrared pyrometers for example, typically have relatively low resolution, so relatively large surface areas of a sample surface are monitored, but typically less than 5 millimeters. Multiple pyrometers may be used to form an array for monitoring several points on a sample. Modern digital IR cameras however, have very high resolution, allowing multiple points of very small areas to be monitored, thus a digital IR camera itself constitutes an IR detector array. Each pixel of a digital IR camera may be "mapped" to a sample point, each corresponding to an area of 100 micrometers or smaller. Some commercially available digital IR cameras allow resolution of 10 micrometers, with further advances in resolution expected.

The IR detector is generally oriented along a focal path substantially perpendicular to that of the source of initiation, i.e. the IR detector is oriented to monitor points on a surface that is substantially perpendicular to the initiation surface. For photopolymerizable samples, the sample may be irradiated from a vertical axis (z axis, perpendicular) to initiate polymerization on a horizontal surface, and the image of a vertical surface of the sample(s) captured from a horizontal direction. Other relative orientations of the IR detector array, the initiation surface and the radiation source (if any) are contemplated and within the scope of the invention. While the relative orientation of the irradiation source and the IR detector need not be exactly 90°, it is preferred that they are oriented within ±45°, more preferably within ±25°, most preferably within ±10°. If desired, an initial thermographic profile, under some preselected initial conditions, may be captured, and then "subtracted" from later captured thermographic profiles, to better illustrate the change in temperature of the samples. For example, the sample may be heated to a first temperature, the thermographic profile captured, and this image subtracted from later thermographic profiles captured during polymerizations.

The IR detector array is generally spaced from the sample(s) at a distance such that the sample substantially fills the field of view. Generally, the detector array is spaced from about 2.54 centimeters to one meter (one inch to 3 feet), depending on the size and number of samples. Fiber optics may be advantageously used if a detector array is to be spaced apart from the experimental apparatus.

By orienting the IR detector array substantially perpendicular to the radiation source, a thermographic profile of a surface of the sample may be obtained. It is generally observed that, after a period of induction, there is a rapid temperature rise represented by a band of elevated temperature that advances through the sample; the band corresponding to the polymerization front. One or more points on the sample may be selected for monitoring. The points may be preselected, or post-selected after capture of the thermographic profile. The temperature of one or more points may be plotted as a function of time, such as during the course of a polymerization, and may be continuously or discontinuously captured. The results from one point may be compared to one or more points on the same sample, or one or more points on a separate sample.

The samples may be mounted on a sample platform or stage. The sample platform may be configured to allow the simultaneous mounting of several samples (an array), and may be configured so as to allow the sample(s) to be moved independently along the x, y and z axes of the platform. The translational movement of the sample stage allows multiple samples to be moved with the field of view of the detector array, and allows sequential sampling of multiple samples. Although not preferred, the thermographic profiles of the samples may be captured through the sample stage provided it is transparent to infrared radiation. Alternatively, if the stage is transparent to the initiating wavelength, photopolymerizable samples may be initiated through the sample stage by the same means. If provided with a heating means, thermally polymerizable samples may be initiated through the sample stage.

Because the samples may be solids, semisolids, viscous liquids or non-viscous liquids, many samples are advantageously handled in a container. Such containers may be of any size or shape, as long as they are configured to accepted samples of the sizes previously described, allow polymerization to be initiated, and the emissive radiation to be monitored and captured. The containers may be selected from materials of known or measured emissivity, non-reactive with the polymerizable samples and are preferably selected from materials IR transparent or semitransparent and possessing low thermal conductivity. Sample chambers may be used to exclude oxygen, or to maintain a controlled atmosphere (such as an inert gas) in a reaction chamber, said chamber being of sufficient dimensions to hold one or an array of samples, and having an IR transmissive window for capturing the thermographic profile of the sample(s). Such chambers may be pressure chambers.

In another embodiment, the sample may polymerized in contact with a three dimensional sample support to simulate coating and curing operations using various monomers, oligomers, initiators, temperatures, and exposure times. In this embodiment, a three dimensional support, such as a mold, may be coated with a polymerizable sample and cured as described herein, with the thermographic profile captured by a IR detector array that is substantially perpendicular to the source of initiation, whether photo- or thermal. The materials used for such three dimensional support may be of any desired size and shape, and be of any material which is thermally stable under the reaction conditions, and nonreactive with the polymerizable sample. The materials described for use with the sample containers supra may be used.

Common IR-transmissive materials include quartz, sapphire, zinc sulfide (ZnS) and selenide (ZnSe), germanium (Ge), arsenic sulfide ($As_2S_3$), gallium arsenide GaAs, indium gallium arsenide (InGaAs), along with a variety of more complicated materials, e.g.: AMTIR-1™ (an amorphous glass of the formula $Ge_{33}As_{12}Se_{55}$, available from Amorphous Materials, Inc, Garland, Tex.). Other classes of infrared transparent materials include simple halide salts, NaCl, NaI etc.; $CaF_2$ being one of the most popular.

When screening an array of polymerizable samples, each such sample is advantageously of the approximately the same size, weight and shape, and in a container (if necessary) of the same material and shape so that any effect of the container may be averaged out. Alternatively, a blank of a non-polymerizable sample in a particular container may be subjected to the reaction conditions, the thermographic profile captured, and subtracted from the polymerizable sample. Applicants have found small oriented polypropylene tubes, i.e. sections of drinking straws, to be suitable.

It will be understood that a thermographic image or profile does not reveal the true temperature of the sample. For non-contact optical methods used to measure temperature, Planck's law for blackbody radiation provides the emission intensity of a "perfect" blackbody as a function of temperature and wavelength. As the polymerizable samples evaluated with the method of the invention are not perfect blackbodies, they emit less radiation at any given wavelength and temperature that Planck's law would predict. The ratio of the actual emission to the predicted blackbody emission is the emissivity, and depends on the wavelength, the temperature as well as the composition of the sample and the surface characteristics.

In many instances it is not necessary to know the actual temperature of the sample. It may suffice to observe that one sample reaches a higher temperature, retains heat longer, cures faster or more uniformly than another sample. Thus the empirical differences in temperatures between samples, or between selected areas or points of a sample may provide the necessary information regarding the sample(s).

If the actual temperature is desired, it may be estimated by measuring the emissivity of a sample, which may be cured, uncured or partially cured at several temperatures, and comparing the results with the thermographic profile obtained during a screening experiment. Other methods of determining the emissivity of a sample, and the actual temperature are disclosed in WO 03/087,885 and U.S. Pat. No. 6,016,190 (Glazman), incorporated herein by reference. Careful calibration would require evaluating emissivity within the container of use.

Simultaneously with the capture of the thermographic profiles, other analytical techniques may be employed to characterize the reactants, products, kinetics or mechanical properties of the samples. For example, IR spectroscopic analysis, preferably Fourier transform IR spectroscopy, may be conducted concurrently with the capturing of the thermographic profile of the samples. In this method, the IR light source and the IR spectroscopic detectors are substantially perpendicular to the IR detector for the thermographic profile. The samples may be contained in an IR transparent container as previously described. Preferably, the IR source and detector are carried through flexible light pipes or fiber-optics for proximity to the sample. In this manner, the conversion of monomers, or the appearance of products or byproducts may be determined by the characteristic IR absorptions, as is known in the art.

In another embodiment, a stress of a sample may be measured while undergoing polymerization while concurrently obtaining a thermographic profile. In this embodiment, the sample may be mounted on strain gauge. Often, polymeric materials shrink upon hardening. This is particularly problematic when the material is in a constrained environment, as in a dental filling or restorative, for example. Dimensional changes upon shrinkage while in a constrained environment can generate a strain within the material that is typically converted into a stress on the surrounding environment (e.g., tooth). Such forces can result in interfacial failures between the tooth and the polymeric material resulting in a physical gap and subsequent microleakage into the tooth cavity. Alternatively, such forces can lead to fractures within the tooth and/or the composite.

Briefly, samples may be bonded to strain gauges (such as those available from Measurements Group, Inc., Micro-Measurements Division, Raleigh, N.C.). The strain gauges may be connected to a scanner (such as an Model 5100A, Vishay Measurements Group, Inc., Instruments Division, Raleigh, N.C.) using a quarter-bridge circuit layout (external dummy). The strain scanner may be connected to a IBM Compatible PC ( ) via a PCI Interface Card (such as Model 5101, Vishay Measurements Group) for real-time acquisition of both strain gauge channels versus time at 10 Hz for 300 seconds per measurement. Results for various may be reported in "microstrain" units with larger values indicative of greater stress and strain within the sample.

FIG. 1 is illustrative of a typical experimental schematic 100 used in the method of the invention. Three-dimensional sample 10 rests on sample stage 12, which may allow for translational movement of the sample or for an array of samples (array not shown) and may optionally have a heat source. Sample 10 may be in a container (not shown), of the size and shape of the sample illustrated, although other sizes and shapes are contemplated, as described). Polymerization of sample 10 is initiated with radiation source 14, such as a UV source, impinging on the top surface of sample 10, with the radiation source 14 connected to power source 16. The radiation (such as UV) may be constrained to all or a portion of the upper, horizontal surface of sample 10 (not shown). The thermographic profile of sample 10 is captured with IR detector array 18, which is illustrated as interfaced with computer 20 for data collection and analysis. IR detector 18 is preferably an IR digital camera, wherein each pixel may be "mapped" to a point on the surface of sample 10 for capture of multiple points. As shown, IR detector 18 is oriented substantially perpendicular to the initiation surface of sample 10. Although a single detector 18 is shown, a plurality of detectors, oriented to different surfaces of sample 10 are contemplated, as described herein.

An initial thermographic profile of sample 10 may be captured (along with any container) for subtraction from later obtained thermographic profiles during polymerization. Data obtained may be collected, and plotted by computer 20. Images may be captured as a function of time, to create a "normalized" video, where the progression of the polymerization front through the sample, and any defects may be noted. This sample may be compared with other samples that vary as to composition of monomers, initiator, exposure time, temperature, etc.

Figure 2:
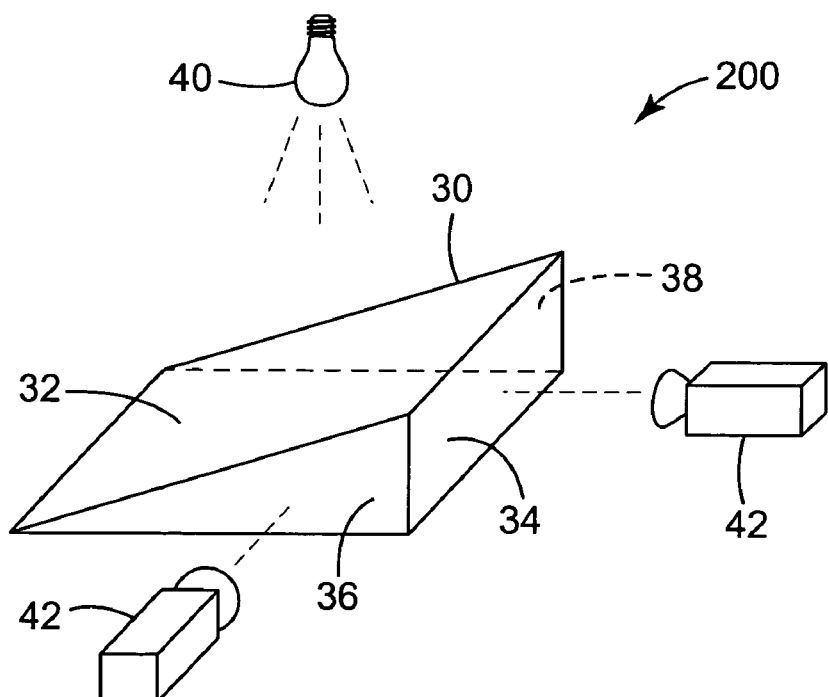
FIG. 2 is a schematic of a sample used in the method of the invention.

FIG. 2 illustrates a particularly useful sample configuration 200. Sample 30 has a variable vertical dimension z, which is nominally collinear with the radiation source 40, and normal to surface 32 and the nominal polymerization front, generated subsequently (not shown). Sample 30 has nominal horizontal dimensions x and y which are anticipated to be coplanar with the polymerization front, and which would be collinear with the optical paths of IR detectors 42. As can be seen, sample 30 varies in the vertical dimension and may further vary in horizontal dimensions x and y (not shown). Sample 30 is nominally wedge-shaped, of variable thickness, and having surfaces 32, 34, 36 and 38. Polymerization is initiated from radiation source 40 on initiation surface 32. Polymerization may be monitored and the thermographic profile captured by IR detectors 42, oriented to surfaces 34 and 36.

In instances where sample 30 is of a constant composition, i.e. the sample does not initially vary through the three-dimensional sample; any of surfaces 34, 36 or 38 may be monitored to captured the thermographic profile of the sample as a function of the thickness of the sample. In other words, the depth of polymerization along axis z may be determined using a sample of variable thickness, such as sample 30.

In another embodiment, sample 30 may vary in composition as well as thickness. In this embodiment, the composition may vary from surface 36 to surface 38. For example, surface 36 may comprise 100% of monomer X and 0% monomer Y, and surface 38 may comprise 0% monomer X and 100% monomer Y, with a gradient concentration of the two monomers therebetween. As before, polymerization may be initiated by radiation source 40 on surface 32. Polymerization of monomer X may by monitored as a function of thickness at surface 36. Concurrently, polymerization of monomer Y may by monitored as a function of thickness at surface 38. Most significantly, the polymerization of the sample may be monitored as a function of composition by capturing the thermographic profile of surface 34, which varies from 100% of monomer X at the edge between surfaces 34 and 36, to 100% monomer Y at the edge between surfaces 34 and 38. This embodiment permits the capture of the thermographic profiles of the polymer X, polymer Y, and the X-Y copolymer simultaneously with an array of three IR detectors. Although not depicted, IR detector 42 may also be oriented to the surface opposite surface 32, though, for example an IR transmissive sample stage. Such samples may also be thermally polymerizable samples.

In addition to samples that vary as a concentration of monomers across the sample, the sample may vary in the type of monomers, oligomers, polymers, or crosslinking agents employed in the sample, or in the type or amount of initiator or catalyst used. Samples having a gradient composition may be prepared using the techniques described in Meredith et al., *Macromolecules,* 2000, 33, pp. 5760-5762 and Meredith et al., *Macromolecules,* 2000, 33, pp. 9747-9756. Essentially, two different components (monomers, oligomers, dissolved polymers, etc) are metered into a beaker at different rates, then mixture drawn into a syringe so that the composition varies essentially linearly along the syringe barrel. A stripe of the material is ejected from the syringe (having varying composition from one side to the other) and drawn out with a knife-edge. The speed of the knife-edge is varied to produce a continual variation in thickness as the material is spread. Thus, the sample varies in thickness on one axis and in composition along another axis, typically the x and y axes where the polymerization is initiated along the z axis as depicted in FIG. 2. It is recognized the described axes are not ideally 90°, as the sample is wedge-shaped, but the axes are still "substantially perpendicular" as described herein.

EXAMPLES

These examples are merely for illustrative purposes only and are not meant to be limiting on the scope of the appended claims. All parts, percentages, ratios, etc. in the examples and the rest of the specification are by weight, unless noted otherwise. All chemicals were obtained from Sigma-Aldrich Chemicals, Milwaukee, Wis. unless otherwise noted. The data has been collected assuming the samples have an emissivity of one.

Table of Abbreviations

| Abbreviation or Trade Designation | Description |
|---|---|
| Z250 | FILTEK Z250 Universal Restorative System commercially available from 3M ESPE, St. Paul, MN |
| Silica Particles | Particles with 123 nanometer mean diameter, commercially available from Nalco Chemical. |
| TONE 201 | ε-caprolactone polyol commercially available from Dow Chemical Company. |
| UVI-6976 | Photoinitiator commercially available from Dow Corporation. |
| EPON 828 | Epoxy resin commercially available from Sartomer Corporation. |
| HEMA | hydroxyethyl methacrylate |
| VAZO 67 | 2,2'-Azobis(2-methylbutyronitrile), a thermal polymerization initiator (ten hour half life temperature 67° C.) available from DuPont, Wilmington DE. |

Example 1

A cylindrical sample (6 mm×1 mm, 75 mg) of Z250 was placed on a glass slide and photocured using a Visilux 2™ Dental Blue light gun (available from 3M Dental Products Division, St. Paul, Min.) held approximately 1 centimeter directly above the sample. A Prism DS™ infrared camera with a 25 millimeter lens (Flir Systems, Boston, Mass.) was held about 46 centimeters (18 inches) away from the sample and temperature data was collected at approximately 10-second intervals. The temperature of the upper surface of the sample as a function of irradiation time is shown in Table 1 below.

TABLE 1

| Elapsed Time (seconds) | Temperature (° C.) |
|---|---|
| 0 | 33.3 |
| 12 | 33.7 |
| 18 | 37.9 |
| 23 | 36.4 |
| 27 | 35.9 |
| 34 | 35.5 |
| 39 | 35.1 |
| 45 | 34.8 |
| 50 | 34.5 |
| 56 | 34.5 |
| 62 | 34.5 |
| 69 | 34.4 |
| 74 | 34.6 |

Example 2

A small disc (6 mm×1 mm, 75 mg) of Z250 was placed on a CEA-06-062WT-120 strain gage (Vishay Measurements) and photocured using a Visilux 2 dental light gun held about 1 centimeter directly above the sample. Irradiation was carried out for 30 seconds. Upon photocuring, shrinkage caused the strain gage to curl up resulting in a signal in the strain gage that is recorded by a computer. The temperature of the sample was simultaneously monitored using a Prism DS camera held about 46 centimeters (18 inches) away from the sample on a tripod. The temperature and strain profile of the sample as a function of irradiation time are shown in Table 2 below. Data from the CEA-06-062WT-120 strain gauge was collected by a Model 5100A Scanner (Vishay Measurements) interfaced with a IBM compatible PC using a Model 5101 PCI Interface Card (Vishay Measurements). Analysis of the digitized signal was done using StrainSmart 5000 software (version 3.10, Vishay Measurements) and is presented in Table 2 as a unitless relative number (A/D means analog-to-digital).

TABLE 2

| Elapsed Time (seconds) | Temperature (° C.) | Strain (A/D Counts) |
|---|---|---|
| 0 | 47.4 | 39 |
| 5 | 47.0 | 283 |
| 13 | 51.7 | 177 |
| 17 | 55.5 | −37 |
| 21 | 55.8 | −220 |
| 27 | 54.9 | −444 |
| 31 | 53.7 | −647 |
| 38 | 53 | −984 |
| 43 | 50.7 | −1108 |
| 47 | 49.7 | −1169 |
| 52 | 48.9 | −1214 |
| 58 | 48.4 | −1252 |
| 62 | 47.7 | −1265 |
| 70 | 47.3 | −1266 |
| 81 | 47.5 | −1308 |
| 86 | 47.5 | −1320 |
| 92 | 47.7 | −1322 |

Example 3

The curing kinetics of a thick section of a composite formulation were studied by recording the heat propagation through the mass using a Prism DS camera. A sample of Z250 was shaped by hand into approximately a cylinder with dimensions 10.9 millimeters×6.7 millimeters. This cylinder was irradiated from the top with a Visulux dental blue light gun (Model 5560) fitted with an aperture of less than 1 millimeter by wrapping the tip of the light gun in perforated aluminum foil to reduce the intensity of light. The gun was held about 1 millimeter from the top of the cylinder to ensure that there was no irradiation of the sides of the cylinder. The thermal imaging camera was held normal to the axis of the cylinder, and upon irradiation the propagation of the exotherm down the axis of the cylinder was observed for 250 seconds at various points along the length of the cylinder. Temperature changes at each time point were obtained by subtracting the original image from all subsequent images obtained during irradiation. The change in temperature at each location as a function of time is shown in Table 3.

Figure 3:
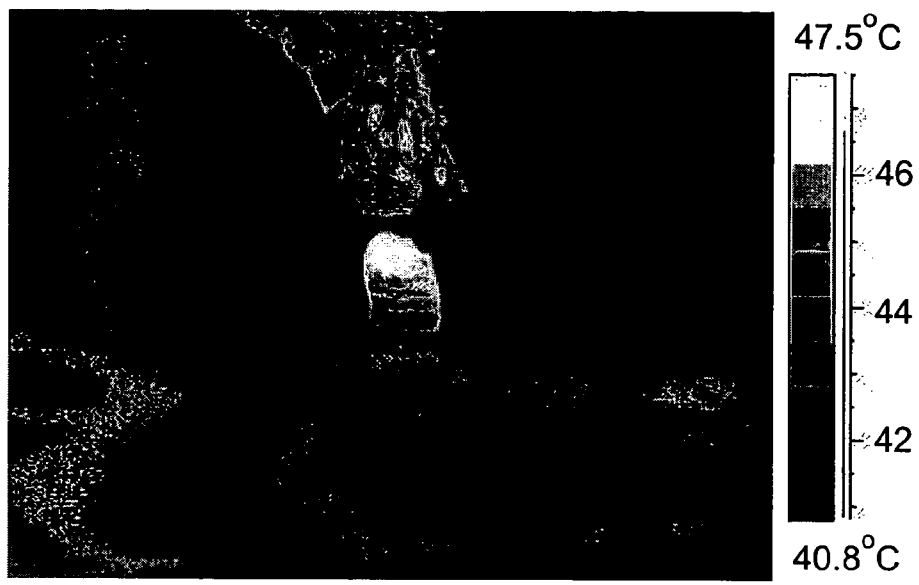
FIG. 3 is a digital image thermographic profile of Example 3.
Figure 4:
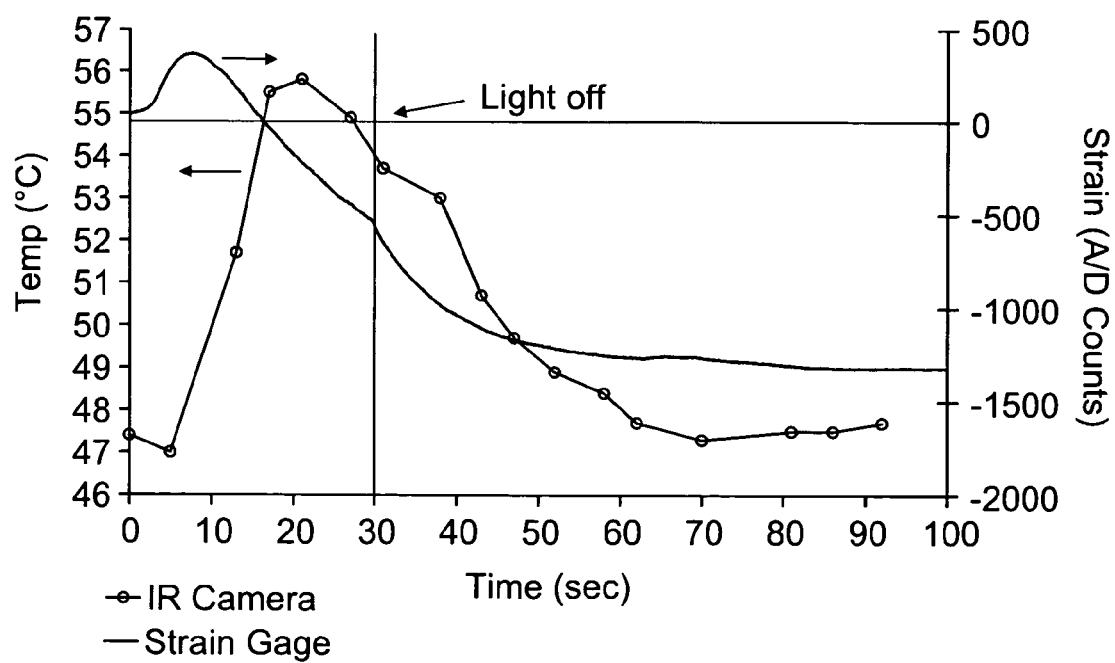
FIG. 4 is a plot of the thermographic profile and strain changes over time of Example 2.
Figure 5:
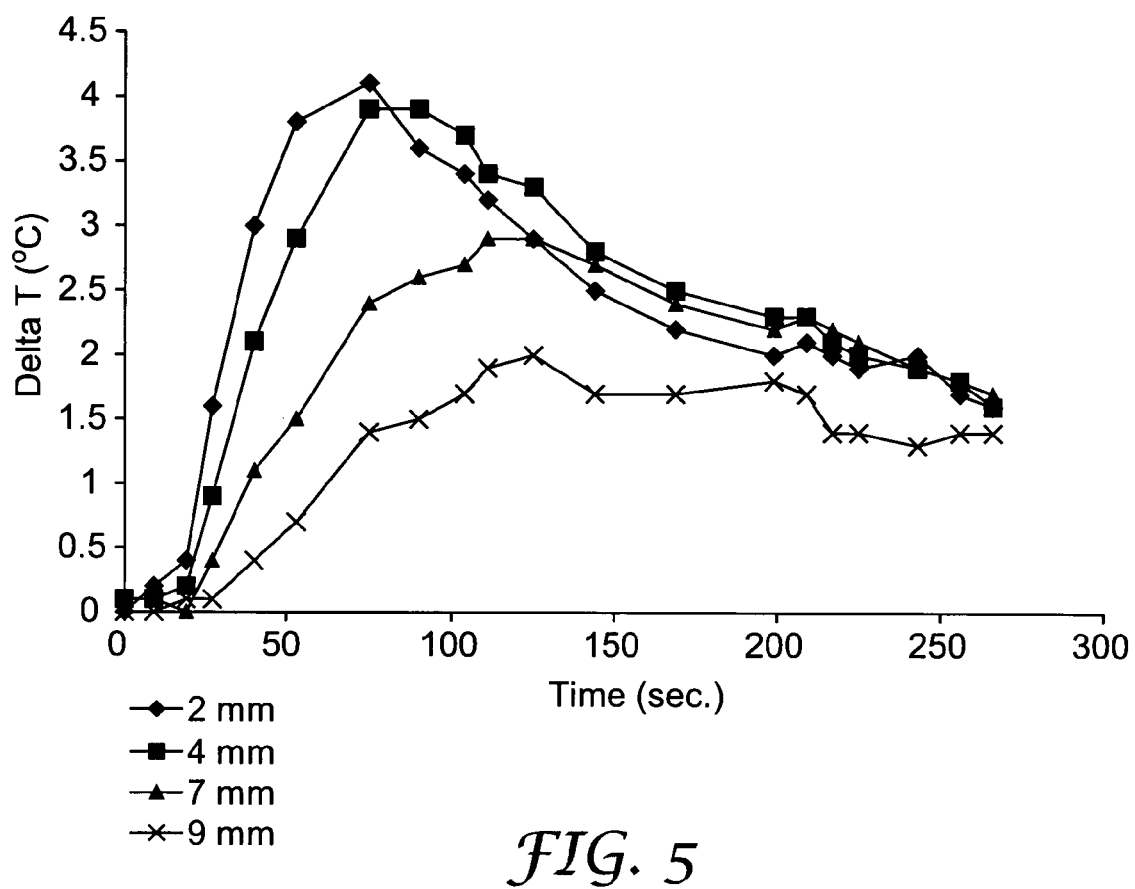
FIG. 5 is a plot of the thermographic profile for various points over time of Example 3.

FIG. 3 is an original, unsubtracted thermographic profile of the sample at 53 seconds elapsed time.

TABLE 3

| Elapsed Time (Seconds) | Temperature Change at 2 mm from top cylinder (° C.) | Temperature Change at 4 mm from top cylinder (° C.) | Temperature Change at 7 mm from top cylinder (° C.) | Temperature Change at 9 mm from top cylinder (° C.) |
|---|---|---|---|---|
| 0   | 0   | 0.1 | 0   | 0   |
| 9   | 0.2 | 0.1 | 0   | 0   |
| 19  | 0.4 | 0.2 | 0.1 | 0.1 |
| 27  | 1.6 | 0.9 | 0.1 | 0.1 |
| 40  | 3   | 2.1 | 0.4 | 0.4 |
| 53  | 3.8 | 2.9 | 0.7 | 0.7 |
| 75  | 4.1 | 3.9 | 1.4 | 1.4 |
| 90  | 3.6 | 3.9 | 1.5 | 1.5 |
| 104 | 3.4 | 3.7 | 1.7 | 1.7 |
| 111 | 3.2 | 3.4 | 1.9 | 1.9 |
| 125 | 2.9 | 3.3 | 2   | 2   |
| 144 | 2.5 | 2.8 | 1.7 | 1.7 |
| 169 | 2.2 | 2.5 | 1.7 | 1.7 |
| 199 | 2   | 2.3 | 1.8 | 1.8 |
| 209 | 2.1 | 2.3 | 1.7 | 1.7 |
| 217 | 2   | 2.1 | 1.4 | 1.4 |
| 225 | 1.9 | 2   | 1.4 | 1.4 |

Example 4

The same procedure used in Example 3 was utilized except that the thermal imaging camera was a CMC Electronics TVS-8500 IR Camera. A sample cylinder of Z250 was prepared with dimensions 10.9 millimeters×6.1 millimeters. This cylinder was irradiated from the top as described in Example 3. The temperatures at these various points as a function of irradiation time are shown in Table 4.

TABLE 4

| Elapsed Time (Seconds) | Temperature at 1 mm from top of cylinder (° C.) | Temperature at 2 mm from top of cylinder (° C.) | Temperature at 5 mm from top of cylinder (° C.) | Temperature at 7 mm from top of cylinder (° C.) | Temperature at 9 mm from top of cylinder (° C.) |
|---|---|---|---|---|---|
| 0   | 23.4  | 23.5  | 23.5  | 23.6  | 23.4  |
| 20  | 31.7  | 30.0  | 26.4  | 24.2  | 23.6  |
| 40  | 31.9  | 31.8  | 29.4  | 26.2  | 24.7  |
| 60  | 31.1  | 31.1  | 30.1  | 27.5  | 26.1  |
| 80  | 30.5  | 30.5  | 30.2  | 28.4  | 26.9  |
| 100 | 29.9  | 30.1  | 30.0  | 28.8  | 27.8  |
| 140 | 29.94 | 29.96 | 29.94 | 29.43 | 28.75 |
| 160 | 29.55 | 29.53 | 29.71 | 29.55 | 28.84 |
| 180 | 29.31 | 29.38 | 29.5  | 29.42 | 28.74 |
| 200 | 29.15 | 29.24 | 29.25 | 29.21 | 28.73 |
| 205 | 29.12 | 29.18 | 29.22 | 29.25 | 28.72 |

Example 5

A dome-shaped portion (measuring 1.0 cm wide×3 mm tall) of Z250 was placed onto a heating plate covered with black electrical tape. The temperature of the dental composite was allowed to equilibrate on top of the hotplate (maintained at 57.7° C.). The dome was then irradiated from the top with a Visulux dental blue light gun (Model 2500) fitted with an aperture of less than 1 millimeter by wrapping the tip of the light gun in perforated aluminum foil to reduce the intensity of light. The gun was held about 1 millimeter from the top of the cylinder. The thermal imaging camera (Prism DS) was held normal to the height axis of the dome, and upon irradiation the temperatures were observed 1.5 mm below the highest point of the material. Temperature changes at each timepoint were obtained by subtracting the original image from all subsequent images obtained during irradiation. The change in temperature as a function of time is shown in Table 5. This example demonstrates the ability to observe a photocure exotherm above an elevated temperature background.

TABLE 5

| Elapsed Time (seconds) | Change in Temperature (° C.) |
|---|---|
| 0  | 0   |
| 21 | 0.4 |
| 31 | 3.3 |
| 36 | 4.6 |
| 40 | 4.4 |
| 47 | 3.4 |
| 53 | 2.8 |
| 57 | 2.5 |
| 65 | 2   |
| 73 | 1.6 |
| 82 | 1.3 |
| 94 | 1   |

Example 6 and Comparative Example C1

A filled epoxy paste was prepared containing 60% by weight Silica Particles, 32% by weight EPON 828, 8% by weight TONE 201 and UVI-6976 (2% by weight relative to resin and filler). The paste was coated at 1 mm thickness onto the outer cylindrical surface of a piece of quartz tubing (9.5 mm OD×6.5 mm ID). The tube was placed sideways onto a stage so that the long axis of the cylinder was parallel to the stage surface and so the face of one circular end was normal to the thermal imaging camera (Prism DS). The coated cylinder was then irradiated from the top (normal to the long axis of the cylinder) using a Lesco™ light source (Super Spot Max, 0.43 W/cm$^2$ of UVA (320-390 nm)). Upon irradiation, temperature changes were observed at 5 equidistant points spanning the entire top half circle of the circular tube end (Point 1 at the furthest left end, Point 3 at the top, and Point 5 at the furthest right end, with 2 and 4 in between). Temperature changes were obtained as a function of time using image subtraction, as in Example 5. The changes are shown for each observation point in Table 6. For Comparative Example C1 the quartz tube was irradiated without the filled epoxy coating and temperature changes at the 5 points were again studied. No point along the top half circle changed more than 5.5° C. upon irradiation over the same time period.

TABLE 6

| Elapsed Time (Seconds) | Temperature Change at Point 1 (° C.) | Temperature Change at Point 2 (° C.) | Temperature Change at Point 3 (° C.) | Temperature Change at Point 4 (° C.) | Temperature Change at Point 5 (° C.) |
| --- | --- | --- | --- | --- | --- |
| 0 | 0 | 0 | 0 | 0 | 0 |
| 3 | 0.3 | 0.1 | 0.1 | 0.2 | 0 |
| 7 | 0.6 | 1.4 | 2.2 | 1.3 | 0.4 |
| 12 | 1 | 2.5 | 4.2 | 2.3 | 0.9 |
| 17 | 1.8 | 4.2 | 6.4 | 4.1 | 1.4 |
| 25 | 3.5 | 7.2 | 11.4 | 7 | 2.9 |
| 29 | 5.3 | 10.3 | 14.3 | 9.7 | 4.5 |
| 38 | 6.9 | 12.6 | 16 | 12.1 | 6.1 |
| 44 | 8.4 | 14.2 | 17.6 | 13.7 | 7.3 |
| 51 | 9.7 | 15.3 | 19.1 | 14.9 | 8.9 |
| 59 | 11.6 | 17.2 | 21.6 | 16.8 | 10.6 |
| 68 | 12.3 | 17.8 | 22.1 | 17.1 | 11.1 |
| 74 | 12.6 | 18.3 | 22.8 | 17.5 | 11.4 |
| 82 | 14 | 20.2 | 24.6 | 19 | 12.5 |
| 91 | 15.5 | 21.9 | 26.4 | 21 | 13.9 |

Example 7

For Example 7, a one percent by weight solution of VAZO 67 was prepared in HEMA. A small quartz cup 7.5 mm in diameter and approximately 8.5 mm deep (approximately 0.36 cm$^3$ internal volume) was loaded with the solution. A strip of aluminum foil tape (3M, St. Paul, Minn.) was placed across the top of the cup and the whole transferred to a hot plate maintained at 87-89° C. The cup was imaged at various time intervals with an infrared camera (Prism DS with 25 mm lens, Flir Systems, Boston Mass.) held at a distance of approximately 28 centimeters (11 inches) for a total of 10 minutes. The time-temperature profile at the midpoint of the cup is shown below in Table 7. The temperature profile at different depths from the top of the cup is presented in Table 8.

TABLE 7

| Elapsed Time (Seconds) | Temperature Change of Solution (° C.) |
| --- | --- |
| 0 | 0 |
| 12 | 3.8 |
| 20 | 8.6 |
| 50 | 15.1 |
| 79 | 19.4 |
| 110 | 24.6 |
| 140 | 32.4 |
| 206 | 42.3 |
| 217 | 43.8 |
| 230 | 47.4 |
| 245 | 53.2 |
| 259 | 60.9 |
| 275 | 115.8 |
| 288 | 112.4 |
| 318 | 78.6 |
| 380 | 49.2 |
| 409 | 44.2 |
| 439 | 41.5 |
| 454 | 40.8 |
| 470 | 40 |
| 485 | 39.8 |
| 500 | 39.5 |
| 581 | 38 |

TABLE 8

| Elapsed Time (Seconds) | Temperature Change at 1 mm from top of cup (° C.) | Temperature Change at 3 mm from top of cup (° C.) | Temperature Change at 5 mm from top of cup (° C.) | Temperature Change at 7 mm from top of cup (° C.) |
| --- | --- | --- | --- | --- |
| 0 | 0 | 0 | 0 | 0 |
| 12 | 1.6 | 2.8 | 4.6 | 5.4 |
| 20 | 6.8 | 7.4 | 9.4 | 10.4 |
| 50 | 12.9 | 13.4 | 16.2 | 16.3 |
| 79 | 16.8 | 17.7 | 20.5 | 21.1 |
| 110 | 22.1 | 23.2 | 25.9 | 25.6 |
| 140 | 33.3 | 33 | 32.5 | 31.9 |
| 206 | 36.5 | 40.7 | 43.2 | 44.3 |
| 217 | 38.2 | 42 | 45.1 | 46.9 |
| 230 | 44.5 | 45.9 | 48.4 | 50.4 |

TABLE 8-continued

| Elapsed Time (Seconds) | Temperature Change at 1 mm from top of cup (° C.) | Temperature Change at 3 mm from top of cup (° C.) | Temperature Change at 5 mm from top of cup (° C.) | Temperature Change at 7 mm from top of cup (° C.) |
|---|---|---|---|---|
| 245 | 47.2 | 51.2 | 54.9 | 56.1 |
| 259 | 49.7 | 56.8 | 64 | 65.2 |
| 275 | 69.5 | 110.2 | 116.8 | 112.4 |
| 288 | 84 | 109.2 | 112.3 | 102.8 |
| 318 | 51.4 | 73.4 | 80.1 | 74.8 |
| 380 | 35.8 | 45.1 | 51.1 | 52.7 |
| 409 | 34.3 | 41.1 | 46 | 48.2 |
| 439 | 32 | 38.6 | 43.2 | 45.8 |
| 454 | 31.8 | 38.2 | 42.7 | 45.4 |
| 470 | 31.4 | 37.5 | 41.9 | 44.4 |
| 485 | 31.3 | 37.3 | 41.4 | 44.1 |
| 500 | 32.5 | 36.9 | 41.1 | 43.5 |
| 581 | 29.3 | 35.4 | 39.6 | 42.4 |

Example 8

The curing kinetics of a thick section of a curing formulation were studied by recording the heat propagation through the mass using a CMC Electronics TVS-8500 IR thermal imaging camera. A sample of Z250 was packed into a cylindrical section (0.7 cm×0.5 cm) of a drinking straw. This cylinder was irradiated from the top with a dental blue light gun (Model 5560) fitted with an aperture of less than 1 millimeter by wrapping the tip of the light gun in perforated aluminum foil to reduce the intensity of light. The gun was held about 1 millimeter from the top of the cylinder to ensure that there was no irradiation of the sides of the cylinder. The thermal imaging camera was held normal to the axis of the cylinder, and upon irradiation the propagation of the exotherm down the axis of the cylinder was observed for 200 seconds at various points along the length of the cylinder. The temperatures of these various points as a function of time are shown in Table 9.

TABLE 9

| Elapsed Time (Seconds) | Temperature at 1.5 mm from top of cylinder (° C.) | Temperature at 3 mm from top of cylinder (° C.) | Temperature at 4.5 mm from top of cylinder (° C.) | Temperature at 6 mm from top of cylinder (° C.) | Temperature at 7.5 mm from top of cylinder (° C.) | Temperature at 9 mm from top of cylinder (° C.) |
|---|---|---|---|---|---|---|
| 0 | 22.2 | 22.2 | 22.3 | 22.3 | 22.3 | 22.3 |
| 10 | 25.4 | 23.9 | 22.9 | 22.6 | 22.3 | 22.4 |
| 20 | 28.7 | 27.8 | 26.2 | 24.4 | 23.1 | 22.8 |
| 30 | 29.6 | 29.8 | 28.4 | 26.5 | 24.5 | 23.6 |
| 40 | 30 | 30.4 | 29.5 | 27.9 | 25.9 | 24.7 |
| 50 | 29.7 | 30.4 | 30 | 28.6 | 26.6 | 25.5 |
| 60 | 29.6 | 30.3 | 30.1 | 28.9 | 27.2 | 26.2 |
| 70 | 29.4 | 30.1 | 30.1 | 29.1 | 27.8 | 26.6 |
| 80 | 29.3 | 29.9 | 30 | 29.2 | 28 | 26.9 |
| 90 | 29.2 | 29.8 | 30 | 29.3 | 28.2 | 27.1 |
| 100 | 29 | 29.6 | 29.8 | 29.4 | 28.1 | 27.2 |
| 110 | 28.8 | 29.4 | 29.6 | 29.3 | 28.3 | 27.3 |
| 120 | 28.6 | 29.2 | 29.5 | 29.1 | 28.2 | 27.3 |
| 130 | 28.5 | 29 | 29.3 | 29 | 28.1 | 27.4 |
| 140 | 28.5 | 28.9 | 29.2 | 28.9 | 28.1 | 27.3 |
| 150 | 28.3 | 28.8 | 28.9 | 28.8 | 28 | 27.2 |
| 160 | 28.3 | 28.7 | 28.8 | 28.7 | 28 | 27.1 |
| 170 | 28.2 | 28.6 | 28.7 | 28.5 | 27.9 | 27 |
| 180 | 28.2 | 28.5 | 28.6 | 28.4 | 27.8 | 27 |
| 190 | 28.2 | 28.5 | 28.6 | 28.3 | 27.7 | 26.9 |
| 200 | 28.2 | 28.4 | 28.5 | 28.3 | 27.5 | 26.9 |

The invention claimed is:

1. A method of monitoring a polymerization in a three-dimensional sample comprising an initiation surface and a separate one or more monitoring surfaces, said monitoring surfaces substantially perpendicular to said initiation surface, wherein the method comprises initiating said polymerization at or on said initiation surface, and capturing a thermographic profile at a plurality of points on at least one monitoring surface of said sample with an infrared detector array.

2. The method of claim 1 wherein said thermographic profile is captured as a function of time.

3. The method of claim 1 wherein said thermographic profile is captured by a digital infrared camera having a plurality of pixels corresponding to points on said sample.

4. The method of claim 1 comprising an array of polymerizable samples.

5. The method of claim 4 wherein said array is simultaneously sampled.

6. The method of claim 4 wherein said array is sequentially sampled.

7. The method of claim 6 wherein the IR detector is repositioned for each sequential sample.

8. The method of claim 6 wherein the array is repositioned for each sequential sample.

9. The method of claim 1 wherein said sample is photochemically polymerizable.

10. The method of claim 1 wherein said polymerizable sample is polymerized to produce thermoplastic, thermoset, elastomeric and thermoplastic elastomeric polymers.

11. The method of claim 1 wherein said polymerizable sample is thermally polymerizable.

12. The method of claim 4 wherein said array is an array of photopolymerizable samples that differ in at least one of
   a) type of photoinitiators,
   b) amount of photoinitiator,
   c) composition of monomer,
   d) intensity of incident radiation;

e) duration of incident radiation;
f) type of additive; and
g) amount of additive.

13. The method of claim 1 wherein said thermographic profile is captured by an IR detector adapted for a plurality of outputs corresponding to the plurality of points on said sample.

14. The method of claim 13, wherein each of said outputs are captured as a function of time.

15. The method of claim 1 wherein the plurality of points are arranged vertically.

16. The method of claim 1 wherein said sample is solid.

17. The method of claim 1 wherein said sample is contained in a sample container.

18. The method of claim 1 further comprising simultaneously measuring stress by mounting said sample in a strain gauge.

19. The method of claim 1 further comprising simultaneously obtaining the infrared spectrum by infrared spectroscopy.

20. The method of claim 1 wherein said sample comprises monomers, which when polymerized, form an interpenetrating polymer network or a semi-interpenetrating polymer network.

21. The method of claim 1 wherein said sample has a vertical dimension z, and horizontal dimensions x and y, and said sample varies in dimension z over at least one of said x and y dimensions.

22. The method of claim 21, wherein the composition of said sample varies over one of said x or y dimensions.

23. The method of claim 1 wherein said sample is in contact with a three dimensional support.

* * * * *

UNITED STATES PATENT AND TRADEMARK OFFICE
CERTIFICATE OF CORRECTION

PATENT NO. : 7,553,670 B2  
APPLICATION NO. : 10/834305  
DATED : June 30, 2009  
INVENTOR(S) : Neal A. Rakow Page 1 of 1

It is certified that error appears in the above-identified patent and that said Letters Patent is hereby corrected as shown below:

Column 7, Line 32 - Delete "b-mercaptopropionic" and insert -- β-mercaptopropionic --, therefor.

Signed and Sealed this

Twenty-seventh Day of October, 2009

David J. Kappos  
*Director of the United States Patent and Trademark Office*